(12) United States Patent
Normand et al.

(10) Patent No.: US 12,092,571 B2
(45) Date of Patent: *Sep. 17, 2024

(54) SOLID-STATE SPECTROMETER

(71) Applicant: Masimo Corporation, Irvine, CA (US)

(72) Inventors: Björn Le Normand, Sollentuna (SE); Åke Forslund, Täby (SE); Björn Danwihl, Vallentuna (SE)

(73) Assignee: Masimo Corporation, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/316,559

(22) Filed: May 12, 2023

(65) Prior Publication Data
US 2023/0384217 A1     Nov. 30, 2023

Related U.S. Application Data

(63) Continuation of application No. 17/383,326, filed on Jul. 22, 2021, now Pat. No. 11,692,934.
(Continued)

(51) Int. Cl.
*G01N 21/3504* (2014.01)
*G01J 3/02* (2006.01)
*G01N 33/00* (2006.01)

(52) U.S. Cl.
CPC ........ *G01N 21/3504* (2013.01); *G01J 3/0208* (2013.01); *G01J 3/0229* (2013.01); *G01J 3/0264* (2013.01); *G01N 33/004* (2013.01)

(58) Field of Classification Search
CPC ...... G01J 3/0208; G01J 3/0229; G01J 3/0264; G01N 2021/3166; G01N 21/314; G01N 21/3504; G01N 21/61
See application file for complete search history.

(56) References Cited

U.S. PATENT DOCUMENTS

| 5,148,239 A | 9/1992 | Magnussen, Jr. et al. |
| 6,021,000 A | 2/2000 | Iizuka et al. |

(Continued)

FOREIGN PATENT DOCUMENTS

| EP | 2065697 A1 | 6/2009 |
| GB | 1482096 | 8/1977 |
| WO | WO 1991/018279 A1 | 11/1991 |

OTHER PUBLICATIONS

Gal, M/Chtanov, A., "Differential optical detection of hydrogen gas in the atmosphere", Sensors and Actuators B, 79 (2001), pp. 196-199.
(Continued)

*Primary Examiner* — Hina F Ayub
(74) *Attorney, Agent, or Firm* — KNOBBE, MARTENS, OLSON & BEAR, LLP

(57) ABSTRACT

A solid-state gas spectrometer for detection of molecules of target gases. An emitter generates light having wavelengths both within and outside of one or more absorption bands of a target molecule. The light provided by the emitter passes through an airway adapter. A reflective beam splitter splits the light transmitted through the airway adapter, into two convergent beams each focused on a light detector. One of the light detectors, which is covered by a filter that rejects light having wavelengths within one or more absorption bands of the target molecule, serves as the sensing detector. The other light detector, which may or may not be covered by a filter, serves as the reference detector. The concentration of a target gas molecule in the gas sample is estimated based on a differential signal that is generated using the signals received from the reference and sensing detectors.

20 Claims, 10 Drawing Sheets

Related U.S. Application Data

(60) Provisional application No. 63/055,803, filed on Jul. 23, 2020.

(56) References Cited

U.S. PATENT DOCUMENTS

| | | |
|---|---|---|
| 6,191,421 B1 | 2/2001 | Yamamori et al. |
| 6,469,303 B1 | 10/2002 | Sun et al. |
| 6,955,652 B1 | 10/2005 | Baum et al. |
| 6,989,549 B2 | 1/2006 | Diekmann et al. |
| 7,157,711 B1 | 1/2007 | Russel |
| 7,235,054 B2 | 6/2007 | Eckerbom |
| 7,244,939 B2 | 7/2007 | Stuttard |
| 7,629,039 B2 | 12/2009 | Eckerbom |
| 9,510,774 B2 * | 12/2016 | Russell .............. G01N 21/3504 |
| 10,532,174 B2 | 1/2020 | Al-Ali |
| 2003/0002044 A1 | 1/2003 | Matthiessen |
| 2006/0009707 A1 | 1/2006 | Daniels et al. |
| 2008/0131111 A1 * | 6/2008 | Messina ............. G02B 19/0066 348/E5.029 |
| 2020/0284654 A1 * | 9/2020 | Sabry ................... G01N 21/031 |
| 2020/0284721 A1 * | 9/2020 | Tortschanoff ...... G01N 21/3504 |
| 2021/0096064 A1 * | 4/2021 | Hietala .................... G01J 3/36 |

OTHER PUBLICATIONS

Massie, Crawford; Stewart. George; McGregpr, George; Gilchist, John R, entitled "Design of a portable optical sensor for methane gas detection", Sensors and Actuators B 113 (2006), pp. 830-836.

Zhang, Guangjun; Li, Yaping; Li, Qingbo, "A miniaturized cabon dioxide gas sensor based on infrared absorption", Optics and Lasers in Engineering 48 (2010), pp. 1206-1212.

Hodgkinson, Jane; Smith, Richard; Ho, Wah On; Saffell, John R.; Tatam, Ralph P., "Non-dispersive infra-red (NDIR) measurement of carbon dioxide at 4.2 um in a compact and optically efficient sensor", Sensors and Actuators B 186 (2013), pp. 580-588.

ISR and Written Opinion for PCT/US2021/042919 dated Oct. 18, 2021, pp. 1-24.

* cited by examiner

SOLID-STATE SPECTROMETER

INCORPORATION BY REFERENCE TO ANY PRIORITY APPLICATIONS

This application is a continuation of U.S. patent application Ser. No. 17/383,326, filed Jul. 22, 2021, entitled "SOLID-STATE SPECTROMETER", which claims the benefit of priority to U.S. Provisional Application No. 63/055,803 filed on Jul. 23, 2020 titled "SOLID-STATE SPECTROMETER". The entire contents of each of the above-identified patent applications are hereby incorporated by reference herein.

FIELD OF THE DISCLOSURE

The present disclosure relates to gas spectrometers and gas analyzers used for monitoring a patient's respiratory system and health, including capnographs and other devices that may be used to monitor patient respiratory gases.

BACKGROUND

Detection and quantification of target gas molecules in a gas sample or a gas stream is critical for a large variety of applications including, but not limited to, medical diagnostic, environmental monitoring, homeland security, industrial monitoring, agricultural monitoring and the like. Providing high level of selectivity, sensitivity, small size, reliability and low-cost manufacturing are highly desirable features for gas sensors used in all these applications. Among various sensing modalities (e.g., electro-chemical, opto-chemical, optical, and the like), spectroscopic techniques that use the unique spectral fingerprints of gas molecules for measuring their concentration, are known for their selectivity, low power consumption and reliability. Spectroscopic gas detection exploits the fact that each gas molecule absorbs light at specific and unique set of wavelength bands. As such, by monitoring the variation of electromagnetic power transmitted through a gas sample, within the absorption wavelength band of a target gas molecule, the concentration of the target gas molecules in the gas sample can be determined.

In respiratory care, it is often desirable to analyze and monitor the composition of a patient's exhaled and/or inhaled breathing gases. One of the most common methods for respiratory gas analysis is a spectroscopic method known as non-dispersive spectroscopy. Non-dispersive spectroscopy enables detection and quantification of specified target gas molecules without using dispersive elements (e.g., prisms, diffraction gratings and the like), to separate out the broadband light into one or more wavelength bands associated within the absorption wavelength bands of the target gas molecule. For most gases, these absorption wavelength bands are located within the infrared (IR) spectral region (e.g., near-IR, mid-IR or far-IR). Nondispersive infrared (NDIR) spectroscopy, as used herein encompasses its broad ordinary meaning known to one of skill in the art, which includes using non-dispersive spectroscopy to detect target molecules (e.g., gas molecules) based on their IR absorption wavelength bands.

NDIR sensors and spectrometers may be used in main flow or sidestream gas analyzers that measure the concentration of target gas molecules directly in the patient's respiratory circuit. $CO_2$ is one of the most relevant respiratory gases that monitoring its concentration (e.g., in exhaled air) is useful in care of critically ill patients undergoing anesthesia or mechanical ventilation as well as in emergency care. For example, measurement of end tidal $CO_2$ can provide useful information such as regarding $CO_2$ production, pulmonary (lung) perfusion, alveolar ventilation, respiratory patterns, and elimination of $CO_2$ from an anesthesia breathing circuit or ventilator. Capnography, as used herein, encompasses its broad ordinary meaning known to one of skill in the art, which includes at least monitoring the concentration or partial pressure of $CO_2$ in respiratory gases and providing real-time information regarding $CO_2$ exhalation and respiratory rates that may be used for rapid and reliable assessment of a patient's ventilatory, circulatory and metabolic function. Thus, capnographers are used in hospitals and other medical institutions for monitoring the condition of a patient's respiratory system, pulmonary perfusion, and metabolism, and are most often used for patients in intensive care and under anesthesia.

In some cases, NDIR sensors and spectrometers may be used in side stream applications where the sample gas is taken out of the main gas circuit, for example using a gas pump, and provided to NDIR sensor or spectrometer for analysis.

NDIR sensors (e.g., gas sensors) can be used in a broad range of non-medical applications to detect and measure the concentration of gas molecules. The non-medical applications of NDIR sensors include but are not limited to: industrial applications, environmental monitoring, homeland security, and military applications. For example, NDIR sensors may be used for monitoring the concentration of certain gas molecules in barns, industrial combustion monitoring, automotive emission monitoring, food storage operations, detection of hazardous gases in public places, detection of chemical agents in battlefield, and the like.

SUMMARY

The system disclosed herein is a non-dispersive (ND) solid-state gas spectrometer for detection of gas molecules in particular mainstream and real-time monitoring the level of certain respiratory gases such as carbon dioxide.

Some embodiments of the disclosed mainstream gas spectrometer operate based on a differential sensing scheme without using any moving parts. A light emitter generates broadband light having wavelengths both within and outside of one or more absorption wavelength bands of a target gas molecule. In some cases, a collimator transforms the light generated by the emitter into a collimated light beam or nearly collimated light beam (e.g., with angle of divergence or convergence less than or equal to ±5 degrees or ±10), that may propagate in a direction different from the propagation direction of the incident light beam. The resulted light beam, that may be collimated, passes through an airway adapter wherein it interacts with a gas stream (e.g., exhaled respiratory gases). A focusing beam splitter divides and focuses the light beam transmitted through the airway adapter into two converging light beams each focused on one light detector from a pair of light detectors that each may be covered by a spectral filter. Each light detector generates an output electric signal proportional to the received optical power. In some examples, the illuminated area on each light detector may be smaller than and fully contained in the sensitive area of the light detector. In some other examples, the illuminated area on each light detector can be larger than the sensitive area of the light detector. The first filter, that covers a first light detector of the pair of light detectors, may only transmit light having wavelengths within one or more absorption wavelength bands of the target gas molecule. The second filter, that covers a second light detector of the pair of light detectors, may only transmit light having wavelengths that are not included in any of the absorption wavelength bands (also referred to as absorption bands) of the target gas molecules. In some other examples, the second filter may only transmit light that is absorbed by the target molecules with a rate that is 10, $10^3$, $10^6$, or $10^9$ times smaller than the absorption rate for the light transmitted by the first filter. In the presence of the first spectral filter (herein referred to as sensing filter), the output of the first light detector serves as a sensing signal. Accordingly, the first light detector covered by the sensing filter is referred to as the sensing detector. The output of the second light detector, which may or may not be covered by a reference filter, serves as the reference signal. Accordingly, the second light detector, is referred to as reference detector. The concentration of the target gas in the portion of gas stream that interacts with the light beam, can be estimated by measuring or calculating the difference or ratio between measured reference and sensing signals. In some examples, the concentration of the target gas may be estimated by calculating a more complicated function of the measured reference and sensing signals.

In some examples, a signal processing module, may generate a differential signal using the measured reference signal and sensing signal wherein the differential signal may be proportional to the difference, ratio or a more complicated function of the reference signal and sensing signal. In some such examples, the differential signal can be used to estimate the concentration of target gas molecules in the portion of gas stream that interacts with the light beam.

In some examples, the differential signal may monotonically decrease or monotonically increase as the concentration of the target gas molecule increases in the airway adapter.

Three notable advantages of the mainstream gas spectrometer according to the present disclosure could be: 1) A single component divides the light beam transmitted through the gas sample and also focuses each one of the resulting light beams on a light detector. 2) The light beam transmitted through the gas sample is divided over its entire cross-section. 3) A significant portion of the energy of each light beam resulted from dividing the transmitted light beam (e.g., larger than 90%, larger than 80%, or larger than 70%), may be focused on the sensitive area of a light detector.

In some examples, the light emitter can be a low-cost thermal emitter (e.g., tungsten wire lamp in a vacuum housing). In some other examples, the light emitter may be a semiconducting optical element (e.g., a semiconductor laser or light emitting diode (LED)). In yet other examples, the emitter can be any light emitter than generates light having wavelengths within one or more absorption wavelength bands of a target molecule.

In some examples, the transmitted light beam passes through a primary filter before being divided by the focusing beam splitter. In some such examples, a reference filter on the reference light detector may not be required to generate a reference signal usable for estimating the concentration of target gas molecules.

In some examples, in the absence of target molecules in the airway adapter, the two beams emerging from the focusing beam splitter, may carry almost the same amount of optical power (e.g., the optical power difference between the two beams can be 5%, 10%, 20% or 30%).

In some examples, the total optical power carried by the two beams emerging from the focusing beam splitter, may be larger than 50%, 70% or 90% of the optical power incident on the focusing beam splitter.

In some examples, the focusing beam splitter, can be a reflective optical element.

In some examples, the focusing beam splitter, can be a segmented mirror.

In some such examples the focusing beam splitter may be a segmented reflective beam splitter comprising two sets of elliptic parabolic reflecting surfaces.

In some examples, the focusing beam splitter, can be a refractive optical element.

In some examples, the collimator, can be a reflective optical element (e.g., a concave mirror such as off-axis parabolic mirror). In some other examples, the collimator can be a refractive optical element (e.g., a positive lens).

In some examples, the collimator can be a refractive optical element (e.g., a positive lens).

Advantageously, using a reflective collimator and/or a reflective beam splitter may enable folding a portion of the optical path within the spectrometer and therefore reducing the size of the spectrometer.

In some examples, the focusing beam splitter alone or in combination with the collimator may function as an anamorphic imager that divides the transmitted light beam into two focused beams each illuminating a region on a detector, the region having a different shape compared to the cross-sectional shape (e.g., an asymmetric shape) of the transmitted light beam. In some such examples, the illuminated area on the detector may have a circular or a square shape.

In some examples, the area of the illuminated region on each detector may be smaller than the sensitive area of the detector by a margin that is larger than the uncertainty associated with the placement of the detector.

In some examples, the focusing beam splitter and/or the collimator may be formed from low cost material and using low cost and high volume manufacturing processes (e.g., metal coating of a plastic substrate formed using injection molding).

In some examples the ND gas spectrometer can be an NDIR spectrometer. Some such NDIR spectrometers may be designed and optimized for detection of gas molecules with strong absorption lines within the spectral region between 1 microns and 12 microns (covering the near-IR and mid-IR and far-IR spectral regions).

In some examples, the solid-state gas spectrometer can be a mainstream NDIR spectrometer that can monitor and measure the concentration of carbon dioxide ($CO_2$) dioxide in inhaled and/or exhaled air by a patient in real time.

In some other examples, the solid-state gas spectrometer may be used to monitor and measure the concentration of one or more target gas molecules in a side stream application where the sample gas is taken out of the main stream (e.g., using a gas pump) and provided to a the solid-state gas spectrometer.

In some cases, the solid-state gas spectrometer can monitor and measure the concentration of two or more target gas molecules, for example, using a focusing beam splitter that divides the light beam transmitted through a gas sample into three or more focused beams wherein one beam illuminates a reference light detector and other beams illuminate multiple sensing light detectors (e.g., each covered by a spectral filter corresponding to one of the target molecules). In these cases, the concentration of each target gas molecule in the portion of gas stream that interacts with the light beam, can be estimated by calculating the difference, ratio or other functions of the measured reference signal and measured sensing signal generated by the sensing detector associated with the target gas molecule (e.g., the sensing light detector that is covered by a filter that only transmits light having wavelengths within one or more absorption wavelength bands of the target molecule).

Various examples of solid-state gas spectrometer and sensing systems that detect and measure the concentration of one or more target molecules in a sample or gas flow are described herein such as the examples enumerated below:

Example 1: An spectrometer configured to analyze constituents in a gas flow, the spectrometer comprising:
  a light emitter configured to emit at least one beam of light;
  a sample chamber adapted for supporting interaction of the beam of light received from the light emitter with the gas flow;
  a first light detector;
  a second light detector; and
  a beam splitter configured to:
    divide the beam of light transmitted though the sample chamber into a first and a second beam of light;
    focus the first beam of light on the first light detector; and
    focus the second beam of light on the second light detector.

Example 2: The gas spectrometer according to example 1, wherein the spectrometer is configured to generate a differential signal using a first signal received from the first light detector and a second signal received from the second light detector.

Example 3: The gas spectrometer according to any of examples 1 and 2, further comprising a collimator configured to transform the beam of light generated by the said light emitter to a collimated beam of light passing through the said sample chamber before being divided by the beam splitter.

Example 4: The gas spectrometer according to example 3, wherein, the collimator is a broadband collimator collimating light having any wavelength within a wavelength range emitted by the light emitter.

Example 5: The gas spectrometer according to any of examples 1 to 4, wherein the light emitter is configured to emit light within a wavelength interval including at least one absorption wavelength band of a target gas molecule.

Example 6: The gas spectrometer according to any of examples 1 to 5, wherein the light emitter is a broadband emitter.

Example 7: The gas spectrometer according to any of examples 1 to 6, wherein the light emitter is a thermal emitter.

Example 8: The gas spectrometer according to any of examples 1 to 7, wherein the light emitter is a tungsten lamp.

Example 9: The gas spectrometer according to any of examples 1 to 8, wherein the first light detector is covered by a first filter.

Example 10: The gas spectrometer according to example 9, wherein the first filter transmits light having wavelengths within at least one of absorption wavelength bands of a target molecule.

Example 11: The gas spectrometer according to example 10, wherein the target molecule is carbon dioxide.

Example 12: The gas spectrometer according to example 11, wherein the absorption wavelength band is located near 4.2 micrometer.

Example 13: The gas spectrometer according to any of examples 1 to 12, wherein the second light detector is covered by a second filter.

Example 14: The gas spectrometer according to example 13, wherein the second filter transmits light having wavelengths not overlapping with any of absorption wavelength bands of a target molecule.

Example 15: The gas spectrometer according to any of examples 2 to 14, wherein the differential signal is a linear or non-linear function of the first signal and the second signal.

Example 16: The gas spectrometer according to any of examples 2 to 13, wherein the differential signal is the ratio between first signal and the second signal.

Example 17: The gas spectrometer according to any of examples 11 to 16, wherein the differential signal is usable for estimating a concentration of carbon dioxide molecules in the sample chamber.

Example 18: The gas spectrometer according to example 3, wherein, the collimator, is a reflective collimator.

Example 19: The gas spectrometer according to example 18, wherein, the collimator, is an off-axis parabolic mirror.

Example 20: The gas spectrometer according to any of examples 1 to 19, further comprising an airway adapter wherein the airway adapter comprises:
  a gas entrance port and a gas exit port;
  the sample chamber, wherein the sample chamber is configured to support the gas flow along a longitudinal direction from the said entrance port to the said exit port;
  an entrance window; and
  an exit window to allow transmission of light through the sample chamber along a transverse direction perpendicular to the said longitudinal direction.

Example 21: The gas spectrometer according to any of examples 1 to 20, further comprising a primary filter that filters light incident on the beam splitter.

Example 22: The gas spectrometer according to any of examples 1 to 21, wherein the beam splitter, is a reflective beam splitter.

Example 23: The gas spectrometer according to example 22, wherein the beam splitter, is a segmented reflective beam splitter.

Example 24: The gas spectrometer according to example 23, wherein the segmented beam splitter, is a concave segmented reflective beam splitter comprising two sets of elliptic parabolic reflecting surfaces.

Example 25: The gas spectrometer according to any of examples 1 to 24, wherein the beam splitter, is a broadband beam splitter that divides light having any wavelength within a wavelength range emitted by the light emitter.

Example 26: The gas spectrometer according to any of examples 1 to 25, wherein in the absence of gas molecules in the sample chamber, the first and second beams of light carry the same amount of optical power.

Example 27: The gas spectrometer according to any of examples 3 to 26, wherein the collimator and the beam splitter together function as an anamorphic imaging system wherein an anamorphic image of a radiative region of the light emitter is formed on each light detector.

Example 28: The gas spectrometer according to any of examples 1 to 27, wherein an area of the illuminated region on each light detector by the first beam of light or second beam of light, is smaller than a sensitive area of the light detector.

Example 29: The gas spectrometer according to any of examples 1 to 28, wherein a received optical power by each light detector is larger than 90% of the sum of the optical power carried by the first beam or the second beam of light.

Example 30: The gas spectrometer according to any of examples 1 to 29, wherein the gas spectrometer is an NDIR spectrometer.

Example 31: The gas spectrometer according to any of examples 1 to 30, wherein the light emitter, the first light detector, the second light detector and the beam splitter are configured for detection of gas molecules with strong absorption lines within the spectral region between 1 and 12 microns (covering the near-IR and mid-IR spectral region, and part of far-IR spectral region).

Example 32: The gas spectrometer according to any of examples 1 to 31, wherein all components of the spectrometer are optimized for real time measurement of a concentration of carbon dioxide molecules in inhaled and/or exhaled air by a patient.

Example 33: A sensing system configured to analyze constituents in a gas flow, the sensing system comprising:
- a light emitter configured to emit at least one beam of light;
- a sample chamber adapted for supporting interaction of the beam of light received from the light emitter with the gas flow;
- a first light detector;
- a second light detector; and
- a beam splitter comprising:
  - a first group of reflecting surfaces configured to redirect and focus a first portion of the beam of light transmitted through the sample chamber on the first light detector; and
  - a second group of reflecting surfaces configured to redirect and focus a second portion of the beam of light received from the said light emitter on the second light detector.

Example 34: The sensing system according to example 33, wherein the sensing system is configured to generate a differential signal using a first signal received from the first light detector and a second signal received from the second light detector.

Example 35: The sensing system according to any of examples 33 and 34, wherein the sensing system is an spectrometer configured to detect molecules in the gas flow based on their absorption wavelength bands.

Example 36: The sensing system according to any of examples 33 to 35, further comprising a collimator configured to transform the beam of light generated by the said light emitter into a collimated beam of light passing through the said sample chamber.

Example 37: The sensing system according to any of examples 33 to 36, wherein the light emitter is configured to emit light within a wavelength interval including at least one absorption wavelength band of a target gas molecule.

Example 38: The sensing system according to any of examples 33 to 37, wherein the light emitter is a thermal emitter.

Example 39: The sensing system according to any of examples 33 to 38, wherein the first group of reflecting surfaces and the second group of reflecting surfaces form a plurality of grooves, and a reflecting surface of the plurality of reflecting surfaces has a parabolic shape.

Example 40: The sensing system according to any of examples 33 to 39, wherein the first light detector is covered by a first filter.

Example 41: The sensing system according to example 40, wherein the first filter transmits light having wavelengths within at least one of absorption wavelength bands of a target molecule.

Example 42: The sensing system according to example 41, wherein the target molecule is carbon dioxide.

Example 43: The sensing system according to example 42, wherein the absorption wavelength band is located near 4.2 micrometer.

Example 44: The sensing system according to any of examples 33 to 43, wherein the second light detector is covered by a second filter.

Example 45: The sensing system according to example 44, wherein the second filter transmits light having wavelengths not overlapping with any of absorption wavelength bands of a target molecule.

Example 46: The sensing system according to any of examples 33 to 45, wherein the differential signal is a linear or non-linear function of the first signal and the second signal.

Example 47: The gas spectrometer according to any of examples 42 to 46, wherein the differential signal is usable for estimating a concentration of carbon dioxide molecules in the sample chamber.

Example 48: The sensing system according to any of examples 33 to 47, wherein in the absence of gas molecules in the sample chamber, a difference between the power carried by the first portion of the beam of light and the power carried by the second portion of the beam of light is less than 5% of the total power carried by the beam of light.

Example 49: The sensing system according to any of examples 36 to 48, wherein the collimator and the beam splitter together function as an anamorphic imaging system and wherein an anamorphic image of a radiative region of the light emitter is formed on each light detector.

Example 50: The sensing system according to any of examples 33 to 49, wherein an area of the illuminated region on each light detector by the first beam of light or second beam of light, is smaller than a sensitive area of the light detector.

Example 51: The sensing system according to any of examples 33 to 50, further comprising an airway adapter wherein the airway adapter comprises:
- a gas entrance port and a gas exit port;
- the sample chamber, wherein the sample chamber is configured to support the gas flow along a longitudinal direction from the said entrance port to the said exit port;
- an entrance window; and
- an exit window to allow transmission of light through the sample chamber along a transverse direction perpendicular to the said longitudinal direction.

Example 52: The sensing system according to any of examples 33 to 51, wherein the first group of reflecting surfaces and the second group of reflecting surfaces form a concave segmented reflector.

Example 53: A sensing system configured to analyze constituents in a gas flow, the sensing system comprising:
- a light emitter configured to emit at least one beam of light;
- a sample chamber adapted for supporting interaction of the beam of light received from the light emitter with the gas flow;
- a first light detector;
- a second light detector; and
- a beam splitter comprising a first plurality of reflecting surfaces and a second plurality of reflecting surfaces, wherein the first and the second plurality of reflecting surfaces form a plurality of grooves, and a reflecting surface of the plurality of reflecting surfaces has a parabolic shape.

Example 54: The sensing system according to example 53, wherein the sensing system is configured to generate a differential signal using a first signal received from the first light detector and the second signal received from the second light detector.

Example 55: The sensing system according to any of examples 53 and 54, wherein the first plurality of reflecting surfaces are configured to redirect and focus a first portion of the beam of light transmitted through the sample chamber on the first light detector; and the second plurality of reflecting surfaces are configured to redirect and focus a second portion of the beam of light transmitted through the sample chamber on the second light detector.

Example 56: The sensing system according to any of examples 53 to 55, wherein the sensing system is an spectrometer configured to detect molecules in the gas flow based on their absorption wavelength bands.

Example 57: The sensing system according to any of examples 53 to 56, further comprising a collimator configured to transform the beam of light generated by the said light emitter to a collimated beam of light passing through the said sample chamber.

Example 58: The sensing system according to any of examples 53 to 57, wherein the light emitter is configured to emit light within a wavelength interval including at least one absorption wavelength band of a target gas molecule.

Example 59: The sensing system according to any of examples 53 to 58, wherein the light emitter is a thermal emitter.

Example 60: The sensing system according to any of examples 53 to 59, wherein the first light detector is covered by a first filter.

Example 61: The sensing system according to example 60, wherein the first filter transmits light having wavelengths within at least one of absorption wavelength bands of a target molecule.

Example 62: The sensing system according to example 61, wherein the target molecule is carbon dioxide.

Example 63: The sensing system according to example 62, wherein the absorption wavelength band is located near 4.2 micrometer.

Example 64: The sensing system according to any of examples 53 to 63, wherein the second light detector is covered by a second filter.

Example 65: The sensing system according to example 64, wherein the second filter transmits light having wavelengths not overlapping with any of absorption wavelength bands of a target molecule.

Example 66: The sensing system according to any of examples 53 to 65, wherein the differential signal is a linear or non-linear function of the first signal and the second signal.

Example 67: The sensing system according to any of examples 62 to 66, wherein the differential signal is usable for estimating a concentration of carbon dioxide molecules in the sample chamber.

Example 68: The sensing system according to any of examples 53 to 67, wherein in the absence of gas molecules in the sample chamber a difference between the power carried by the first portion of the beam of light and the power carried by the second portion of the beam of light is less than 5% of the total power carried by the beam of light.

Example 69: The sensing system according to any of examples 57 to 68, wherein the collimator and the beam splitter together function as an anamorphic imaging system wherein an anamorphic image of a radiative region of the light emitter is formed on each light detector.

Example 70: The sensing system according to any of examples 53 to 69, wherein an area of the illuminated region on each light detector by the first beam of light or second beam of light, is smaller than a sensitive area of the light detector.

Example 71: The sensing system according to any of examples 53 to 70, further comprising an airway adapter wherein the airway adapter comprises:
 a gas entrance port and a gas exit port;
 the sample chamber, wherein the sample chamber is configured to support gas flow along a longitudinal direction from the said entrance port to the said exit port;
 an entrance window; and
 an exit window to allow transmission of light through the sample chamber along a transverse direction perpendicular to the said longitudinal direction.

Example 72: The sensing system according to any of examples 53 to 71, wherein the first plurality of reflecting surfaces and the second plurality of reflecting surfaces form a concave segmented reflector.

Example 73: A sensing system configured to analyze constituents in a sample, the sensing system comprising:
 a light emitter configured to emit at least one beam of light;
 a sample chamber adapted for supporting interaction of the beam of light received from the light emitter with the sample;
 a first light detector;
 a second light detector; and
 a segmented reflector comprising:
  a first group of reflecting surfaces configured to redirect and focus a first portion of the beam light transmitted through the sample chamber on the first light detector; and
  a second group of reflecting surfaces configured to redirect and focus a second portion of the beam light the beam light transmitted through the sample chamber on the second light detector.

Example 74: The sensing system according to example 73, wherein the sensing system is configured to generate a differential signal using a first signal received from the first light detector and a second signal received from the second light detector.

Example 75: The sensing system according to any of examples 73 and 74, wherein the sensing system is an spectrometer configured to detect molecules in the sample based on their absorption wavelength bands.

Example 76: The sensing system according to any of examples 73 to 75, wherein the differential signal is usable for estimating a concentration of a target molecule in the sample chamber.

Example 77: The sensing system according to any of examples 73 to 76, further comprising a collimator configured to transform the beam of light generated by the said light emitter to a collimated beam of light passing through the said sample chamber.

Example 78: The sensing system according to any of examples 73 and 77, wherein the sample is a gas sample.

Example 79: The sensing system according to any of examples 73 and 76, wherein the sample is a liquid sample.

Example 80: A sensing system configured to analyze constituents in a sample, the sensing system comprising:
 a light emitter configured to emit at least one beam of light;

a sample chamber adapted for supporting interaction of the beam of light received from the light emitter with the sample;
a first light detector;
a second light detector; and
a beam splitter comprising:
   a first group of reflecting surfaces configured to redirect and focus a first portion of the beam of light transmitted through the sample chamber on the first light detector, and
   a second group of reflecting surfaces configured to redirect and focus a second portion of the beam of light transmitted through the sample chamber on the second light detector,
   wherein the beam splitter does not comprise a dispersive element.

Example 81: The sensing system according to example 80, wherein the sensing system is configured to generate a differential signal using a first signal received from the first light detector and a second signal received from the second light detector.

Example 82: The sensing system according to any of examples 80 and 81, wherein the sensing system is an spectrometer configured to detect molecules in the sample based on their absorption wavelength bands.

Example 83: The sensing system according to any of examples 80 to 82, wherein the differential signal is usable for estimating a concentration of a target molecule in the sample chamber.

Example 84: The sensing system according to any of examples 80 to 83, further comprising a collimator configured to transform the beam of light generated by the said light emitter into a collimated beam of light passing through the said sample chamber.

Example 85: The sensing system according to any of examples 80 to 84, wherein the sample is a gas sample.

Example 86: The sensing system according to any of examples 80 to 84, wherein the sample is a liquid sample.

Example 87: A sensing system configured to analyze constituents in a sample, the sensing system comprising:
a light emitter configured to emit at least one beam of light;
a sample chamber adapted for supporting interaction of the beam of light received from the light emitter with the sample;
a first light detector;
a second light detector;
a third light detector; and
a segmented reflector comprising:
   a first group of reflecting surfaces configured to redirect and focus a first portion of the beam light transmitted through the sample chamber on the first light detector;
   a second group of reflecting surfaces configured to redirect and focus a second portion of the beam light transmitted through the sample chamber on the second light detector; and
   a third group of reflecting surfaces configured to redirect and focus a third portion of the beam light received from the said light emitter on the third light detector.

Example 88: The sensing system according to example 87, wherein the sensing system is configured to generate a first differential signal using a first signal received from the first light detector and a third signal received from the third light detector and a second differential signal using a second signal received from the second light detector and a third signal received from the third light detector.

Example 89: The sensing system according to any of examples 88, wherein the first differential signal is usable for estimating a concentration of a first target molecule in the sample chamber and the second differential signal is usable for estimating a concentration of a second target molecule in the sample chamber.

Example 90: The sensing system according to any of examples 87 to 89, wherein the first light detector is covered by a first filter and the second light detector is covered by a second filter.

Example 91: The sensing system according to example 90, wherein the first filter transmits light having wavelengths within at least one of absorption wavelength bands of the first target molecule and wherein the second filter transmits light having wavelengths within at least one of absorption wavelength bands of the second target molecule Example 92: The sensing system according to example 91, wherein the third light detector is covered by a third filter and wherein the third filter transmits light having wavelengths not overlapping with any of absorption wavelength bands of the first target molecule and the second target molecule.

Example 93: The sensing system according to any of examples 87 to 92, further comprising a collimator configured to transform the beam of light generated by the said light emitter to a collimated beam of light passing through the said sample chamber.

Example 94: The sensing system according to any of examples 87 to 93, wherein the sample is a gas sample.

Example 95: The sensing system according to any of examples 87 to 93, wherein the sample is a liquid sample.

Example 96: A sensing system configured to analyze constituents in a gas flow, the sensing system comprising:
a light emitter configured to emit at least one beam of light;
a sample chamber adapted for supporting interaction of the beam of light received from the light emitter with the gas flow;
a first light detector;
a second light detector; and
a beam splitter comprising:
   a lens configured to transform the beam of light transmitted through the sample chamber to a convergent beam of light; and
   a beam splitter configured to receive the convergent beam of light, redirect a first portion of the convergent beam of light on the first light detector; and redirect a second portion of the convergent beam of light on the second light detector.

Example 97: A sensing system configured to analyze constituents in a gas flow, the sensing system comprising:
an a light emitter configured to emit at least one beam of light;
a sample chamber adapted for supporting interaction of the beam of light received from the light emitter with the gas flow;
a first light detector;
a second light detector; and
a beam splitter comprising a waveguide, said waveguide comprising:
   an input waveguide segment configured to receive the beam of light transmitted through the sample chamber, guide a first portion of the beam of light into a first output waveguide segment, and guide a second portion of the beam of light into a second output waveguide segment;

wherein an exit port of the first output waveguide segment is aligned to illuminate the first light detector, and an exit port of the second output waveguide segment is aligned to illuminate the second light detector.

Example 98: A method of analyzing constituents in a gas flow, the method comprising:

transmitting a beam of light emitted by a light emitter through the gas flow;

redirecting and focusing a first portion of the beam of light transmitted through the gas flow on a first light detector;

redirecting and focusing a second portion of the beam of light transmitted through the gas flow on a second light detector; and analyzing constituents in the gas flow based on a first signal received from the first light detector and a second signal received from the second light detector.

Example 99: The method according to example 98, further comprising, by an electronic processor connected to the first light detector and the second light detector: generating a differential signal using a first signal received from the first light detector and a second signal received from the second light detector.

Example 100: The method according to any of examples 98 and 99, wherein analyzing constituents in the gas flow comprises detecting molecules in the gas flow based on their absorption wavelength bands.

Example 101: The method according to any of examples 98 to 100, further comprising transforming the beam of light generated by the said light emitter into a collimated beam of light before transmitting the beam of light through the said sample chamber.

Example 102: The method according to any of examples 98 to 101, wherein the light emitter is configured to emit light within a wavelength interval including at least one absorption wavelength band of a target gas molecule.

Example 103: The method according to any of examples 98 to 102, wherein the light emitter is a thermal emitter.

Example 104: The method according to any of examples 98 to 103, wherein redirecting and focusing the first portion and the second portion of the beam of light comprises reflecting the beam of light transmitted through the gas flow off of a concave segmented reflector.

Example 105: The method according to example 104, wherein the segmented reflector comprises a first group of reflecting surfaces and a second group of reflecting surfaces.

Example 106: The method according to example 105, wherein the a first group of reflecting surfaces and the second group of reflecting surfaces form a plurality of grooves, and a reflecting surface of the first group of reflecting surfaces or the second group of reflecting surface has a parabolic shape.

Example 107: The method according to any of examples 98 to 106, wherein the first light detector is covered by a first filter.

Example 108: The method according to example 107, wherein the first filter transmits light having wavelengths within at least one of absorption wavelength bands of a target molecule.

Example 109: The method according to 108, wherein the target molecule is carbon dioxide.

Example 110: The method according to example 109, wherein the absorption wavelength band is located near 4.2 micrometer.

Example 111: The method according to any of examples 98 to 110, wherein the second light detector is covered by a second filter.

Example 112: The method according to example 111, wherein the second filter transmits light having wavelengths not overlapping with any of absorption wavelength bands of a target molecule.

Example 113: The method according to any of examples 99 to 112, wherein the differential signal is a linear or non-linear function of the first signal and the second signal.

Example 114: The method according to any of examples 99 to 113, wherein the differential signal is usable for estimating a concentration of carbon dioxide molecules in the gas flow.

Example 115: The method according to any of examples 98 to 114, wherein in the absence of gas molecules in the sample chamber, a difference between the power carried by the first portion of the beam of light and the power carried by the second portion of the beam of light is less than 5% of the total power carried by the beam of light.

Example 116: The method according to any of examples 101 to 115, wherein transforming the beam of light generated by the said light emitter into the collimated beam of light comprises reflecting the beam of light off of an off-axis parabolic mirror.

Example 117: The method according to any of examples 98 to 116, wherein redirecting and focusing the first portion and the second portion of the beam of light on the first and the second light detector comprises forming an anamorphic image of a radiative region of the light emitter on each light detector.

Example 118: The method according to any of examples 98 to 117, wherein an area of the illuminated region on each light detector by the first beam of light or the second beam of light, is smaller than a sensitive area of the light detector.

Example 119: The method according to any of examples 98 to 118, wherein the gas flow is supported by a sample chamber of an airway adapter, the sample chamber configured to enable interaction of the beam of light emitted by the light emitter with the gas flow.

Example 120: The method according to examples 119, wherein the airway adapter comprises:

a gas entrance port and a gas exit port;

an entrance window, and an exit window to allow transmission of light through the sample chamber along a transverse direction perpendicular to a longitudinal direction; and wherein the sample chamber is configured to support the gas flow along a longitudinal direction from the said entrance port to the said exit port.

Example 121: A method of analyzing constituents in a sample, the method comprising:

transmitting a beam of light emitted by a light emitter through a sample chamber adapted for supporting interaction of the beam of light received from a light emitter with the sample;

redirecting and focusing a first portion of the beam of light transmitted through the sample chamber on a first light detector; and redirecting and focusing a second portion of the beam of light transmitted through the sample chamber on a second light detector.

analyzing constituents in the sample based on a first signal generated by the first light detector and a second signal generated by the second light detector.

Example 122: The method according to example 121, further comprising, by an electronic processor connected to the first light detector and the second light detector: generating a differential signal using a first signal received from the first light detector and a second signal received from the second light detector.

Example 123: The method according to any of examples 121 and 122, wherein analyzing constituents in the sample comprises detecting molecules in the sample based on their absorption wavelength bands.

Example 124: The method according to any of examples 121 to 123, further comprising transforming the beam of light generated by the said light emitter into a collimated beam of light before transmitting the beam of light through the said sample chamber.

Example 125: The method according to any of examples 121 to 124, wherein the light emitter is configured to emit light within a wavelength interval including at least one absorption wavelength band of a target molecule.

Example 126: The method according to any of examples 121 to 125, wherein the light emitter is a thermal emitter.

Example 127: The method according to any of examples 121 to 126, wherein redirecting and focusing the first portion and the second portion of the beam of light comprises reflecting the beam of light transmitted through the sample off of a concave segmented reflector.

Example 128: The method according to example 127, wherein the segmented reflector comprises a first group of reflecting surfaces and a second group of reflecting surfaces.

Example 129: The method according to example 128, wherein the a first group of reflecting surfaces and the second group of reflecting surfaces form a plurality of grooves, and a reflecting surface of the first group of reflecting surfaces or the second group of reflecting surface has a parabolic shape.

Example 130: The method according to any of examples 121 to 129, wherein the first light detector is covered by a first filter.

Example 131: The method according to example 130, wherein the first filter transmits light having wavelengths within at least one of absorption wavelength bands of a target molecule.

Example 132: The method according to 108, wherein the target molecule is carbon dioxide.

Example 133: The method according to Example 132, wherein the absorption wavelength band is located near 4.2 micrometer.

Example 134: The method according to any of examples 121 to 133, wherein the second light detector is covered by a second filter.

Example 135: The method according to example 134, wherein the second filter transmits light having wavelengths not overlapping with any of absorption wavelength bands of a target molecule.

Example 136: The method according to any of examples 122 to 135, wherein the differential signal is a linear or non-linear function of the first signal and the second Example 137: The method according to any of examples 122 to 136, wherein the differential signal is usable for estimating a concentration of carbon dioxide molecules in the gas flow.

Example 138: The method according to any of examples 121 to 137, wherein in the absence of molecules in the sample chamber a difference between the power carried by the first portion of the beam of light and the power carried by the second portion of the beam of light is less than 5% of the total power carried by the beam of light.

Example 139: The method according to any of examples 124 to 138, wherein transforming the beam of light generated by the said light emitter into the collimated beam of light comprises reflecting the beam of light off of an off-axis parabolic mirror.

Example 140: The method according to any of examples 121 to 139, wherein redirecting and focusing the first portion and the second portion of the beam of light on the first and the second light detector comprises forming an anamorphic image of a radiative region of the light emitter on each light detector.

Example 141: The method according to any of examples 121 to 140, wherein an area of the illuminated region on each light detector by the first beam of light or the second beam of light, is smaller than a sensitive area of the light detector.

Example 142: A sensing system configured to analyze constituents in a gas flow, the sensing system comprising:
  a light emitter configured to emit at least one beam of light;
  a sample chamber adapted for supporting interaction of the beam of light received from the light emitter with the gas flow;
  a first light detector;
  a second light detector; and
  a beam splitter comprising:
    a first group of reflecting surfaces configured to redirect and focus a first portion of the beam of light transmitted through the sample chamber on the first light detector; and
    a second group of reflecting surfaces configured to redirect and focus a second portion of the beam of light received from the said light emitter on the second light detector.

Example 143: The sensing system according to example 142, wherein the sensing system is configured to generate a differential signal using a first signal received from the first light detector and a second signal received from the second light detector.

Example 144: The sensing system according to any of examples 142 and 143, wherein the light emitter is a thermal emitter.

Example 145: The sensing system according to any of examples 142 to 144, wherein the first group of reflecting surfaces and the second group of reflecting surfaces form a plurality of grooves, and a reflecting surface of the plurality of reflecting surfaces has a parabolic shape.

Example 146: The gas spectrometer according to any of examples 142 to 145, wherein the differential signal is usable for estimating a concentration of carbon dioxide molecules in the sample chamber.

Example 147: The gas spectrometer according to any of examples 142 to 146, further comprising a collimator configured to transform the beam of light generated by the said light emitter to a collimated beam of light passing through the said sample.

Example 148: The sensing system according to any of examples 142 to 147, further comprising an airway adapter wherein the airway adapter comprises:
  a gas entrance port and a gas exit port;
  the sample chamber, wherein the sample chamber is configured to support the gas flow along a longitudinal direction from the said entrance port to the said exit port;
  an entrance window; and
  an exit window to allow transmission of light through the sample chamber along a transverse direction perpendicular to the said longitudinal direction.

Example 149: The sensing system according to any of examples 147 and 148, further comprising an enclosure wherein the light emitter, the first light detector, the second light detector and the beam splitter are placed in the enclosure.

Example 150: The sensing system according to example 149, wherein the airway adapter is integrated with the enclosure.

Example 151: The sensing system according to example 150, wherein the airway adapter is a removable component and can be detached from the enclosure.

Any of the above Examples or Additional Examples can be combined.

DETAILED DESCRIPTION

Figures 1A, 1B:
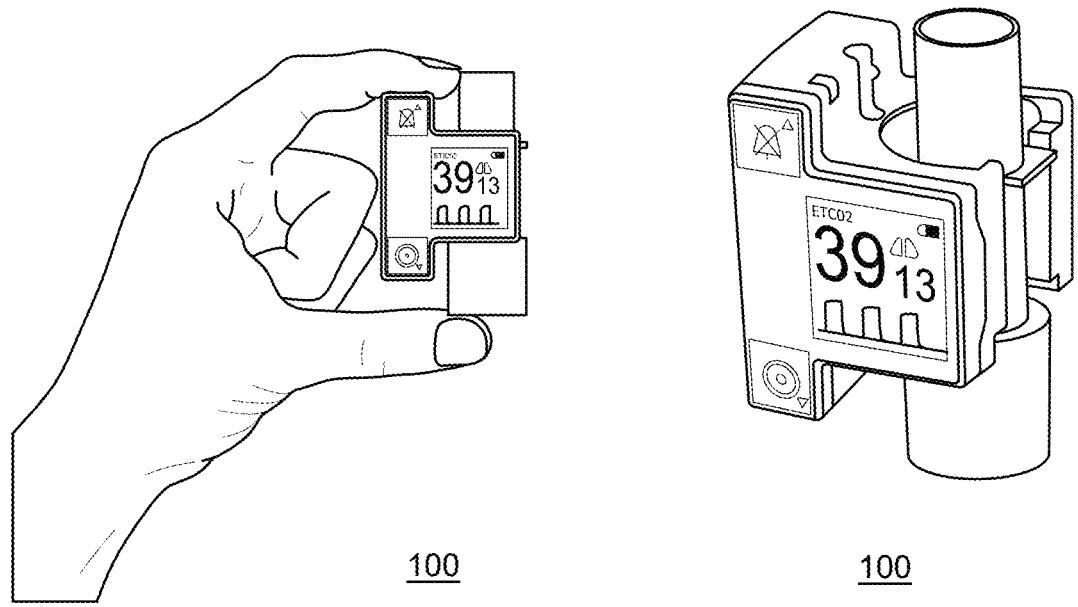
FIGS. 1A and 1B are photographs of an example solid-state mainstream gas spectrometer.

Non-dispersive spectroscopy is a technique for detection and quantification of specific target molecules (e.g., target gas molecules) without using dispersive elements (e.g., prisms, diffraction gratings and the like), to separate out the broadband light (or broadband electromagnetic radiation) into one or more wavelength bands associated with the absorption wavelength bands of a target molecule. In some cases, where the absorption wavelength bands of a target molecule is located within the infrared (IR) spectral region (e.g., near-IR, mid-IR or far-IR), the technique may be referred to as Nondispersive infrared (NDIR) spectroscopy. NDIR as used herein encompasses its broad ordinary meaning known to one of skill in the art, which includes using non-dispersive spectroscopy to detect target molecules based on their IR absorption wavelength bands.

Most NDIR based sensing systems and spectrometers use a broadband light source and one or more filters and light detectors to selectively measure transmitted optical power within spectral regions that overlap with one or more absorption wavelength bands of a target gas molecule. The accuracy of these NDIR sensors and spectrometers can be adversely affected by optical power changes not related to the concentration of target gas molecules as well as the level of optical power transmitted through the gas sample and delivered to the light detectors.

Differential sensing, for example, can eliminate the impact of detected power variations that are not associated with concentration of a target molecule in the gas sample. In a differential sensing scheme, a portion of the light wave, which is transmitted through the gas sample, is provided to a first light detector and another portion to a second light detector. The first light detector, herein referred to as sensing detector, may be covered by a spectral filter (referred to as sensing filter) that only transmits light having wavelengths in one or more absorption wavelength bands of the target molecule. Thus, the signal generated by the sensing detector may be only correlated with light having wavelengths in the one or more absorption wavelength bands of the target molecule. In some examples, the second light detector, herein referred to as reference detector, may be covered by a spectral filter (referred to as reference filter) that only transmits light having wavelengths not included in one or more absorption wavelength bands of the target molecule. Thus the signal generated by the reference detector may not be correlated with light having wavelengths included in one or more absorption wavelength bands of the target molecule. In some other examples, the reference detector may not be covered by a reference filter. In these examples, the signal generated by the reference detector may correlated with light having wavelengths both within and outside of the one or more wavelength bands of the target molecule. The concentration of the target molecules in the gas sample can be estimated by measuring the difference, or the ratio between the signals generated by the sensing and reference detectors. The sensing and reference detectors may have similar or different spectral responses. In some examples, the concentration of the target molecules in the gas sample may be estimated by calculating a function of the signals generated by the sensing and reference detectors (e.g., a linear or a non-linear function).

The accuracy and reliability of the differential technique mentioned above may depend on the spatial overlap between the portions of light received by the sensing detector and the reference detector particularly in part of their trajectories that pass through and interact with the sample gas molecules (e.g., passing through a gas chamber or airway adapter). In some examples, to eliminate variations that are not associated with concentration of a target molecule in the gas sample, the portions of light received by the sensing and the reference detectors, may pass through the same optical path, controlled by the same optical components and interact with the same region of the gas sample. In some other examples, wherein portions of light provided to sensing and reference detectors do not have sufficient spatial overlap within the gas sample, the changes of the resulting differential signal may be at least partially associated with variations that are not related to the concentration of the target gas molecule in a gas sample.

A second aspect that affects the signal-to-noise ratio of the differential output in an NDIR spectrometer, is the level of optical power received by the sensing and reference detectors. In some cases, the signal-to-noise ratio may be proportional to the magnitude to of optical power that interacts with the gas molecules and is received by the sensing and reference detectors. As such, in these examples, the signal-to-noise ratio and therefore the accuracy of gas analysis may be improved if a larger portion of the optical power that interacts with the gas molecules is received by the reference and sensing detectors.

To maximize the spatial overlaps, in some gas analyzers, the entire light beam that passes through the gas sample can be divided by a large transmissive beam splitter into two beams. The first beam is transmitted toward the reference detector and the second beam is reflected toward the sensing detector. However, in the absence of a separate focusing element, the diameter of the light beams emerging from the beam splitter can be larger than the sensitive area of the detectors resulting is loss of a significant portion of the optical power. Further, the beam splitting element (e.g., a transmissive beam splitter) may dissipate a portion or the received optical power.

Advantageously, the solid-state gas spectrometer disclosed herein employs an improved beam splitter that not only divides the entire light beam passing through the gas sample with low power dissipation, but may also focus a large portion of the power carried by each resulting beam on the corresponding detector (e.g., a portion larger than 90%, 80%, or 70%). Using this beam splitter and a new optical configuration, the disclosed designs can beneficially reduce optical loss and improve the signal-to-noise ratio of the measurement compared to existing differential gas spectrometers (e.g., NDIR gas spectrometer).

The solid-state gas spectrometer system as described herein can be integrated in a compact and low-cost device with which target gases occurring in the respiratory care, can be analyzed by a main flow measuring process with high level of sensitivity and accuracy and low level of power consumption.

Advantageously, employment of reflective optical elements in the disclosed designs may enable fabrication of more compact gas spectrometers.

Some embodiments of the solid-state gas spectrometer disclosed herein are NDIR spectrometers that can measure the concentration of $CO_2$ molecules and therefore may be used as capnographs.

It should be noted that the solid-state gas sensor configurations described herein can be used with a variety of gas sensing systems. The examples provided in this document are non-limiting examples of such system adapted to detect the presence and measure the concentration of one or more gas species in a main flow respiratory gas analyzer used for monitoring the health of a patient.

Figure 1C:
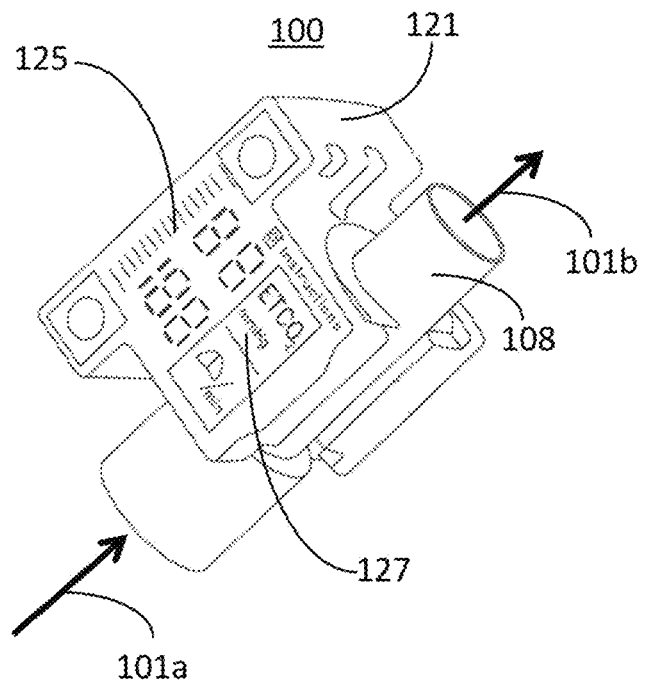
FIG. 1C is a schematic diagram illustrating a three-dimensional view of the solid-state mainstream gas spectrometer shown in part A and B.

FIGS. 1A and 1B illustrate an example solid-state mainstream gas spectrometer. FIG. 1C illustrates a three-dimensional view of the solid-state mainstream gas spectrometer shown in FIG. 1A and FIG. 1B. The solid-state mainstream gas spectrometer 100 comprises an airway adapter 108 and a housing 121. The housing 121, houses a spectrometer (e.g., an NDIR spectrometer), electronic circuitry for processing the signals generated by the spectrometer and a user interface that may include a display 125 for displaying the measurement results (e.g., concentration of a target gas, flow rate and the like) and a control panel 127 to allow the user to adjust and/or select measurement parameters. In some examples, the display 125 can be a touchscreen display that may allow the user to adjust and/or select measurement parameters.

Figure 2:
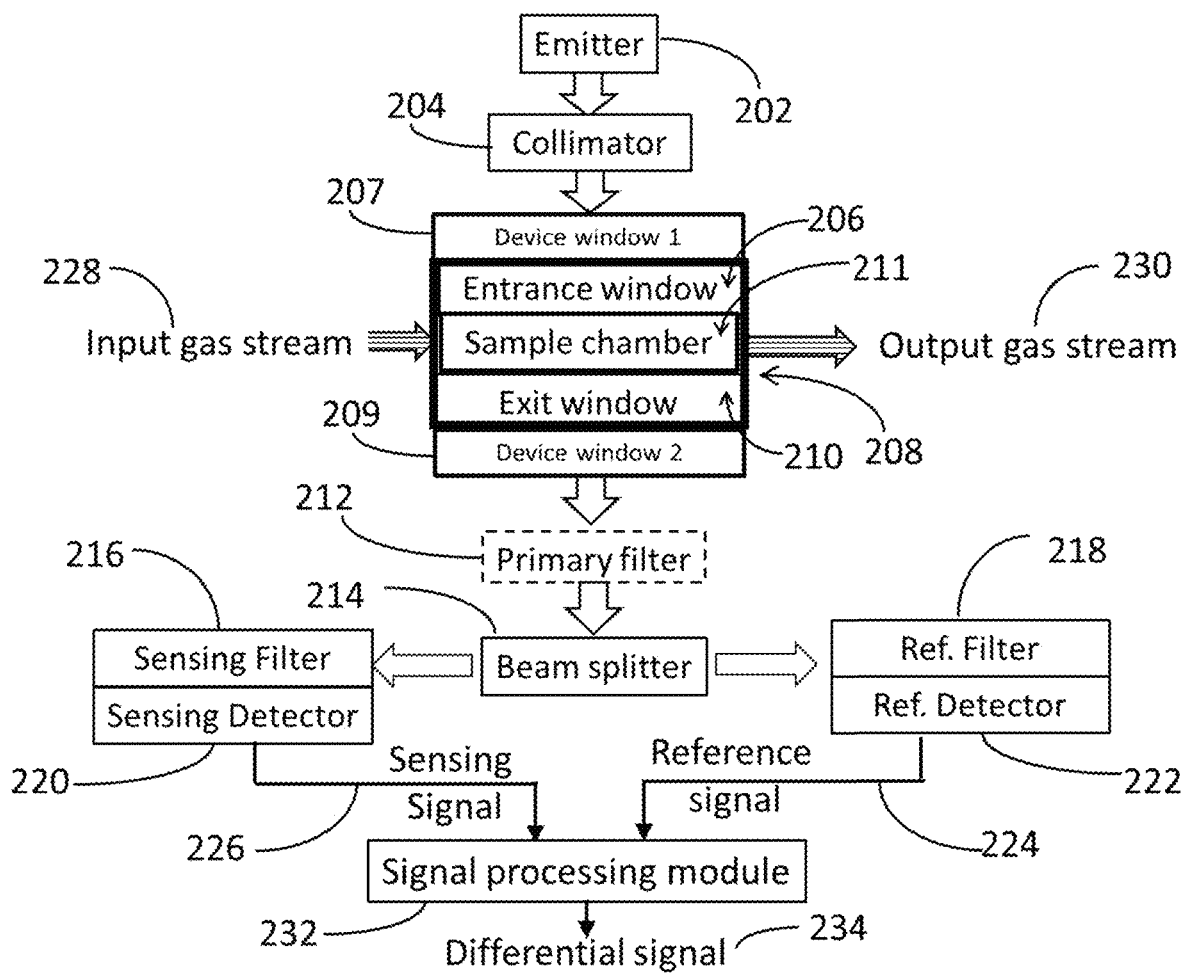
FIG. 2 is a diagram illustrating an example solid-state mainstream gas spectrometer in accordance with certain aspects of the present disclosure.

FIG. 2 is a diagram illustrating an example sensing system 200 for detecting and quantifying molecules in a sample (e.g., gas sample or liquid sample). The optical system 200 can be a gas spectrometer in accordance with certain aspects of the present disclosure. A light emitter 202 (e.g., a thermal emitter, a laser diode or a light emitting diode and the like) generates light with a broad emission spectrum. The spectral power distribution of the emitted light may be non-uniform with a peak wavelength located in near-infrared (NIR), mid-infrared (MIR) spectral region or far-infrared (FIR). For example, the peak wavelength can be between 1000 nm and 1500 nm, 1500 nm and 2000 nm, 2000 nm and 2500 nm, 2500 nm and 3000 nm, 3500 nm and 4000 nm, 4000 nm and 4500 nm, 4500 nm-5000 nm, 5000 and 8000 nm, 8000 and 9000 nm, 9000 nm and 12000 nm. The spectral power distribution of the emitted light may overlap with one or more absorption lines of one or more target gas molecules. In certain embodiments the light emitter 202 may be selected such that the peak wavelength of its emission spectrum is close (e.g., within ±50 nm, ±100 nm, ±500 nm or ±1000 nm) to the peak wavelengths of the selected one or more absorption lines of one or more target gas molecules. In some examples, the light emitter 202 can emit light with temporally varying intensity. For example, light emitter may emit light with periodically varying intensity. Such modulated intensity may enable using noise reduction techniques (e.g., lock-in measurement) to improve the signal-to-noise ratio of the detected signals.

In some examples, a collimator 204, may transform the divergent light beam emitted from the emitter 202 to a collimated light beam. In some such examples, the beam reflected (or transmitted) by the collimator may be nearly collimated. For example, the beam reflected (or transmitted) by the collimator can be a convergent or divergent beam with a convergence or a divergence angle of, for example, less than 5 degrees or less than 10 degrees. Advantageously, collimating the light beam emitted by the emitter 202 allows efficient spectral filtering in the subsequent stages (e.g., by reducing the angular width of the beams incident on the filters). The collimated light beam passes through a first device window 207, enters an airway adapter 208 through its entrance window 206, passes through the sample chamber 211 of the airway adapter 208 and exits the airway adapter 208 through its exit window 210. Inside the sample chamber 211, of the airway adapter 208, the light beam interacts with gas molecules passing through the sample chamber 211. The gas molecules inside the sample chamber 211 are continuously replenished by an input gas stream 228 (e.g., exhaled respiratory gas by a patient) entering the sample chamber 211 and output gas stream 230 exiting the sample chamber 211.

In presence of molecules that can absorb light within the wavelength range of emitted light, the power of the transmitted light through the chamber may be attenuated due to absorption by certain molecules (e.g., target gas molecules). The transmitted light beam exits the airway adapter 208 through an exit window 210 and then passes through a second device window 209. In some cases, the airway adapter 208 (that includes an entrance window 206, a sample chamber 211 and an exit window 210) is a detachable component that is integrated with the main device to provide an optical path from the first device window 206 to the second device window 209, through the sample chamber 211. In some examples, the power of transmitted light may be also attenuated due to reflection and/or absorption by the entrance/exit windows 206/208 and/or the first and second device windows 207/209. In some other examples, the power attenuation due to reflection by the chamber windows 206/208 and the device windows 207/209 may be minimized by coating one or more antireflection layers on one or both sides of each one of these windows.

In some examples, the light beam exiting the exit window 210 may pass through a primary filter 212 that attenuates light having wavelengths not included in its passband. The passband of the primary filter 212 may include spectral regions both overlapping and not overlapping with one or more absorption bands of the target molecule. Next, a beam splitter 214 transforms the light beam transmitted through the airway adapter 208, into a first light beam and a second light beam each carrying a portion of the power carried by the incident light beam. The ratio between the magnitude of the optical power carried by the first and second light beams may be 50/50, 60/40, 70/30 or other ratios. In some such examples, the total optical power carried by the first and second beams may be less than the optical power of the light beam transmitted through the airway adapter 208. In some examples, the beam splitter may transform the collimated incident beam into two converging beams propagating along two different directions. Subsequently, the first light beam emerging from the beam splitter illuminates a sensing detector 220 (e.g., a light detector or a photodetector) covered by a sensing filter 216 and the second light beam emerging from the beam splitter illuminates a reference detector 222 (e.g., a light detector or a photodetector) that may be covered by a reference filter 218. In some examples, wherein the light beam passes through a primary filter 212 before being split by the beam splitter 214, a reference filter may not exist on the reference detector. Advantageously, the beam splitter may be designed to divide the entire light beam passing through the sample chamber 211 into two beams (e.g., converging beams), wherein each beam only illuminates the sensitive area the detector on which the beam is incident. Each one of the detectors 220/222 can be a light detector or photodetector that generates an electric signal (e.g., current or voltage) proportional to the optical power incident on the sensitive area of the detector. The sensing detector 220 and the reference detector 222 may have identical spectral responses. The sensing filter 216 can be a bandpass filter that only transmits light having wavelengths within one or more absorption bands of the target molecules. The reference filter 218 can be a bandpass filter that only transmits light that cannot be absorbed by the target molecules. In some other examples, the reference filter may only transmit light that is absorbed by the target molecules with a rate that is 10, $10^3$, $10^6$, or $10^9$ times smaller than the absorption rate for the wavelengths transmitted by the sensing filter.

In some examples, the sensing signal 226 generated by the sensing detector 220 may monotonically decrease as the concentration of target gas molecules in the sample chamber 211 of the airway adapter 208 increases. In some examples, where the reference detector is covered by a reference filter 218, the reference signal 224 generated by the reference detector 222 can be independent of the concentration of target gas molecules in the sample chamber 211 of the airway adapter 208. In these examples, the sensing and reference signals 224/226 may vary by the same amount due to factors not related to the concentration of target gas molecules in the sample chamber 211. For example, variation of the emitted power by the emitter or variation of the alignment between various optical components may change the sensing signal 226 and reference signal 224 by the same exact value.

Figure 3A:
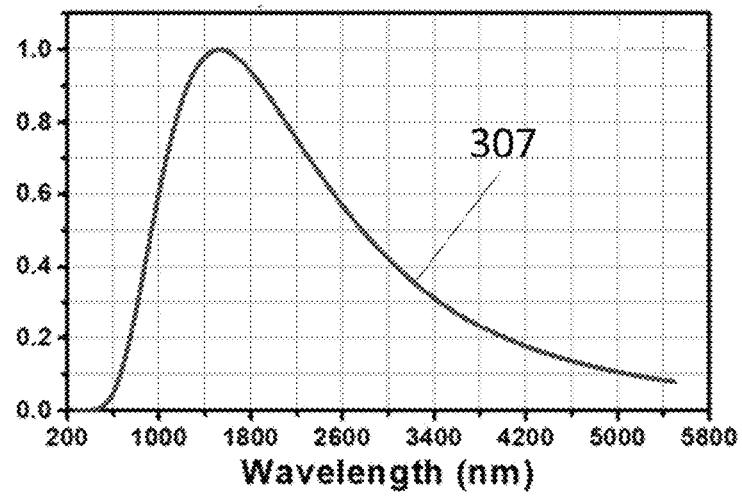
FIG. 3A illustrates the power spectrum of an example thermal light emitter that may be used as the light source in the solid-state mainstream gas spectrometer.

In some examples, the light emitter 202 may be a thermal emitter. FIG. 3A illustrates the power spectrum 307 of an example thermal emitter (e.g., a tungsten lamp) that emits light with wavelengths primarily between 500 nm and 6000 nm with a peak emission near 1600 nm. A thermal emitter may be used, for example, for measuring the concentration of carbon dioxide molecules in a gas stream (e.g., exhaled respiratory gases). Accordingly, the mainstream gas spectrometer 200 can measure the concentration of carbon dioxide in its sample chamber 211 using a thermal emitter as the light emitter. More specifically, the collimator 204, first device window 207, entrance window 206, exit window 210, second device window 210, the primary filter 212, beam splitter 214, the sensing 216 and reference 218 filters, and the sensing 220 and reference 222 detectors may be designed and/or selected to differentially monitor the absorption of IR light across a wavelength range covering one or more absorption wavelength bands of the carbon dioxide ($CO_2$) molecule. In some other examples, the light emitter 202 and all the optical components may be designed and/or selected to differentially monitor the absorption of IR light across a wavelength range covering one or more absorption wavelength bands of other gas molecules that a relevant for medical diagnostic and monitoring a patient's health condition; for example, 02, carbon dioxide, nitric oxide anesthetic agents (e.g., halothan, nitrous oxide, enflurane and the like). For example, all the windows may transmit light having a wavelengths between 2000 nm and 5000 nm, 5000 nm and 7000 nm, 7000 nm and 9000 nm, and 9000 nm and 12000 nm with low loss (e.g., less than 50%, less than 30%, or less than 10%). In some cases, the primary filter 212 may be eliminated from the spectrometer 200. In some other examples the reference filter 218 may be eliminated from the spectrometer 200.

In some embodiments, the spectrometer 200 may be used to analyze a sample of molecules provided to the sample chamber 211 without the need for a continuous flow of molecules through the sample chamber 211. In some such embodiments, the output gas stream 230 may not exist and input gas stream 228 may provide a finite volume of gas molecules to the sample chamber 211. Once a set amount of sample is provided to the sample chamber 211 (e.g., a set pressure is established inside the chamber), the input gas stream is discontinued, the chamber is closed, and the sample trapped within the chamber is analyzed. In some examples (e.g., side stream applications), the sample may be a gas sample taken out of a main gas circuit, an environment, collected from a patient's exhalation and provided to the sample chamber 211 for analysis.

In some embodiments, the sensing system 200 may be used to analyze a liquid sample. In some cases the liquid sample may flow through the sample chamber 211 while in other cases, a volume of liquid sample may be injected to the sample chamber 211 for analysis.

Figure 3B:
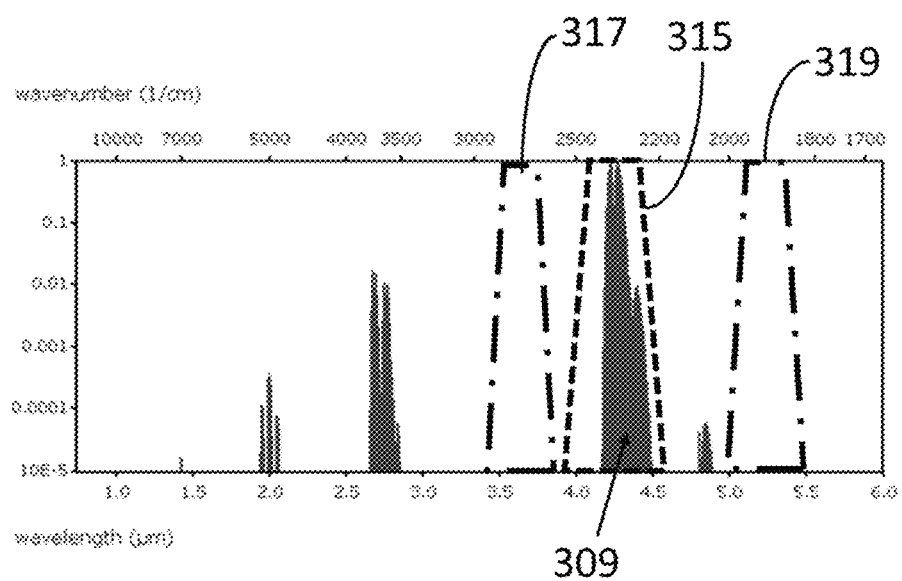
FIG. 3B illustrates the spectrum of the absorption wavelength bands of carbon dioxide molecule within wavelength range of 1 to 5 microns. The wavelength regions defined by the dashed and dash-doted boxes depict example pass bands of the filters covering the sensing and reference light detectors respectively.

FIG. 3B illustrates the spectrum of the absorption bands of carbon dioxide between 1 and 5 microns. For example, a band pass filter 315 (defined by the dashed line) with pass band spanning the wavelength interval between 4 microns and 4.5 microns may be used as the sensing filter 216 to measure the amount of light absorbed by the $CO_2$ absorption band 309 centered at or near 4.3 microns. To eliminate the changes of transmitted power not related to the concentration of the $CO_2$ molecules, a reference filter 218 with a pass band 317 (defined by dash-dotted line) spanning the wavelength interval between 3.4 microns and 3.9 microns can be used. Alternatively, the reference filter 218 may have a pass band 319 spanning the wavelength interval between 5 microns and 5.5 microns. Note that, the pass bands of any of the reference filters shown do not overlap with any of $CO_2$ absorption wavelength bands and they are limited to wavelengths within the emission spectrum 307 of the thermal emitter.

Figure 4A:
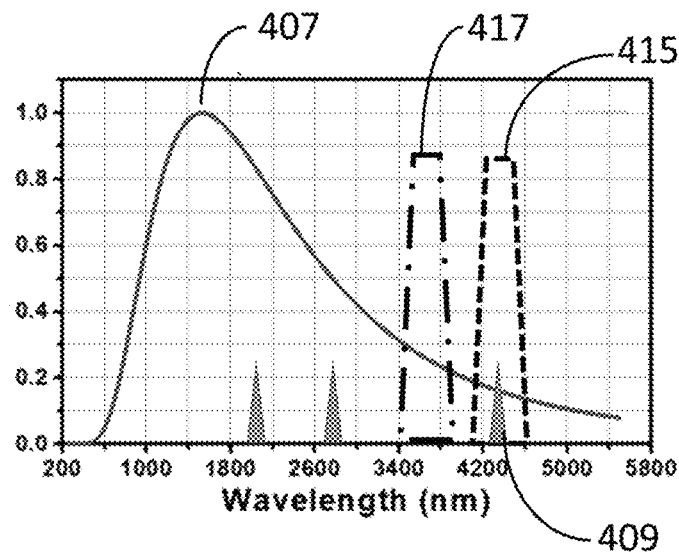
FIG. 4A illustrates the overlap between the spectrum of an example thermal emitter and absorption bands of $CO_2$ molecule between 1 and 5 microns.
Figure 4B:
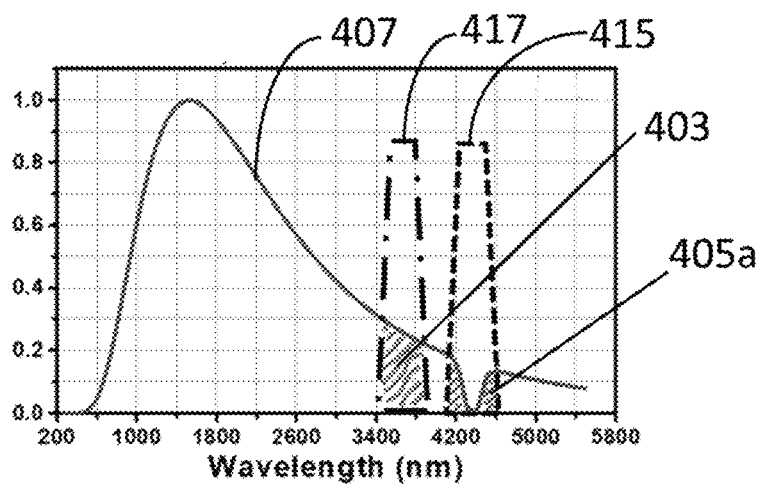
FIG. 4B illustrates received optical power integrated over the pass band of the sensing filter (dashed box) and the reference filter (dash-dotted box) in the presence of $CO_2$ molecules in the examined gas sample.
Figure 4C:
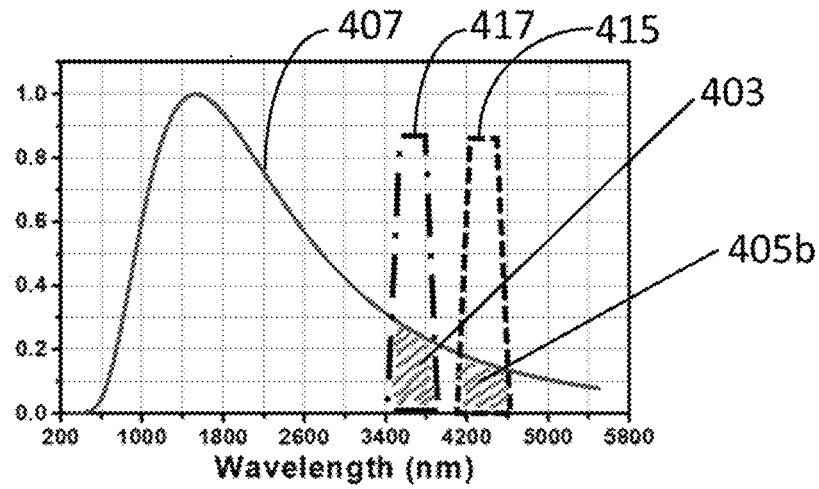
FIG. 4C illustrates received optical power integrated over the pass band of the sensing filter (dashed box) and the reference filter (dash-dotted box) in the absence of $CO_2$ molecules in the examined gas sample.

FIG. 4A illustrates the alignment between the spectrum 407 of the thermal emitter, the absorption band 409 of the $CO_2$ molecule near 4.3 microns, the spectral response 417 of the reference filter 218, and the spectral response 415 of the sensing filter 216. FIG. 4B illustrates the integrated power 405a over the pass band 415 of the sensing filter 216 and the integrated power 403 over the pass band 417 of the reference filter 218 in the presence of $CO_2$ molecules in the sample chamber 211. FIG. 4C illustrates the integrated power 405b over the passband 415 of the sensing filter 216 and the integrated power 403 over the passband 417 of the reference a filter 218 in absence of $CO_2$ molecules in the chamber 211. The sensing detector 220 covered by the sensing filter 216, generates a sensing signal 226 proportional to the integrated power over the pass band 415 of the sensing filter 216. The reference detector 222 covered by the reference filter 218, generates a reference signal 224 proportional to the integrated power over the pass band 417 of the reference filter 216.

As shown in FIG. 4B and FIG. 4C, the presence and absence of $CO_2$ molecules only reduce the sensing signal 226 and leave the reference signal 224 unchanged. It should be appreciated that a change in the ratio between sensing signal 226 and reference signal 224 may only depend on the change of the concentration of target gas molecules (e.g., $CO_2$ molecules) in chamber 211 because the beam splitter is designed to divide the entire cross-section of the transmitted light beam through the sample chamber 211.

The sensing signal 226 and the reference signal 224 may be received by a signal processing module 232. The signal processing module generates a differential signal 234 that may only vary in response to a change in the concentration of gas molecules in the chamber. In some examples, the differential signal 234 may monotonically decrease as the concentration of gas molecules in the chamber increase. In some other examples, the differential signal 234 may monotonically increase as the concentration of gas molecules in the chamber increase The differential signal 234 may not change in response to changes not associated with the concentration of target molecules in the sample chamber 211 (e.g., variations of the emitter power). In some examples, the differential signal 234 may be the ratio between the sensing signal 226 and reference signal 224. In some other examples, the differential signal 234 may be the difference between the sensing signal 226 and reference signal 224. In yet other examples, the differential signal 234, may any linear or nonlinear function of the sensing signal 226 and the reference signal 224.

The signal processing module 232 may be an electronic circuit that is designed to or can be programed to process the received sensing signal 226 and reference signal 224 to generate a differential signal 234. In some examples, the signal processing module 232 may include a non-transitory memory and a hardware processor that can execute machine executable instructions. The hardware processor may be any type of general purpose central processing unit ("CPU"). In some embodiments, the signal processing module 232 may include a processor of any type including, but not limited to complex programmable logic devices ("CPLDs"), field programmable gate arrays ("FPGAs"), application-specific integrated circuits ("ASICs") or the like.

In some examples, the emitter 202 is a continuous wave emitter. In some other examples, the power of light emitted by the emitter 202 can periodically vary in time (e.g., with sinusoidal, square, triangular or other temporal profiles), for example, by modulating the driving current (or voltage) of the emitter. In these examples, a lock-in amplifier may be used to generate and measure the differential signal 234 to further increase the signal-to-noise ratio of the differential signal 234.

Figure 5A:
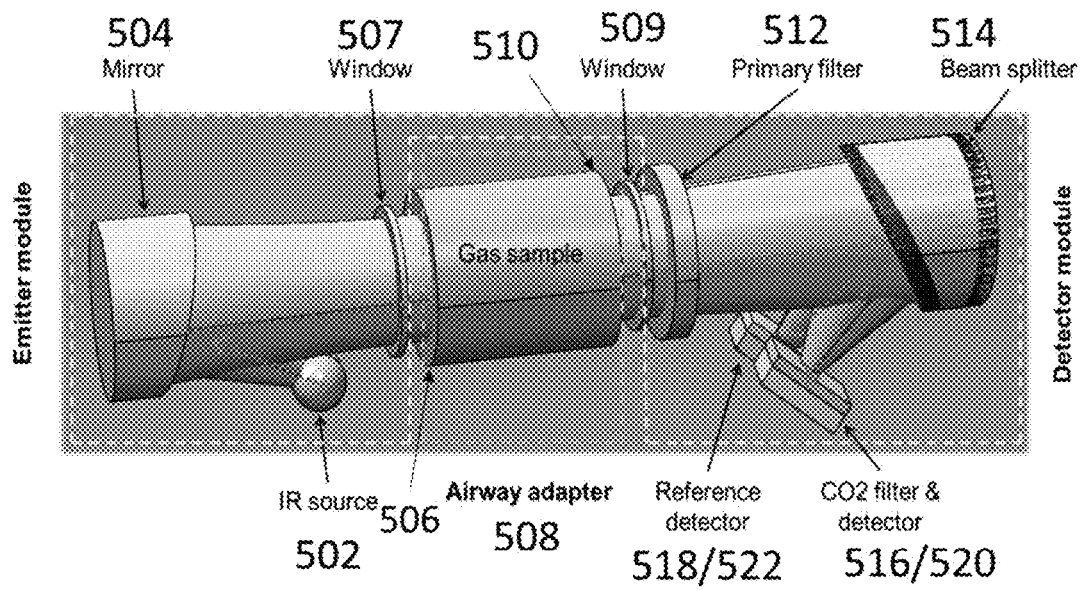
FIG. 5A illustrates a perspective view of the arrangement of optical components and the light beams in an embodiment of the mainstream solid-state gas spectrometer in accordance with certain aspects of the present disclosure.

FIG. 5A illustrates a perspective view of the arrangement of optical components and the light beams in an embodiment of a mainstream solid-state gas spectrometer in accordance with certain aspects of the present disclosure. In this embodiment, the light emitter 502 is placed in front of a concave mirror 504 (e.g., an off-axis parabolic mirror) that transforms the divergent beam emitted by the emitter 502 into a reflected collimated light beam (or near collimated with divergence less than 5 or 10 degrees) propagating toward the airway adapter 508. In some examples, the collimating optical element can be a positive lens. Advantageously, using a concave mirror as the collimating element, may facilitate the optical alignment of the system (e.g., by enabling alignment using visible light)

The light beam reflected by the concave mirror 504 passes through the first device window 507, the entrance window 506 and the chamber of the airway adapter 508, exits through the exit window 510, and passes through the second device window 509. The light transmitted through the sample gas flowing through the airway adapter 508 becomes incident on a reflective focusing beam splitter 514. In some examples, the light transmitted through the sample gas flowing through the airway adapter 508, may pass through a primary filter 512 before becoming incident on a reflective focusing beam splitter 514. In some such examples, the primary filter can be a wideband filter, for example, made by combing a short-pass filter and a long-pass filter. In other examples, the primary filter can be a bandpass filter.

Figure 5B:
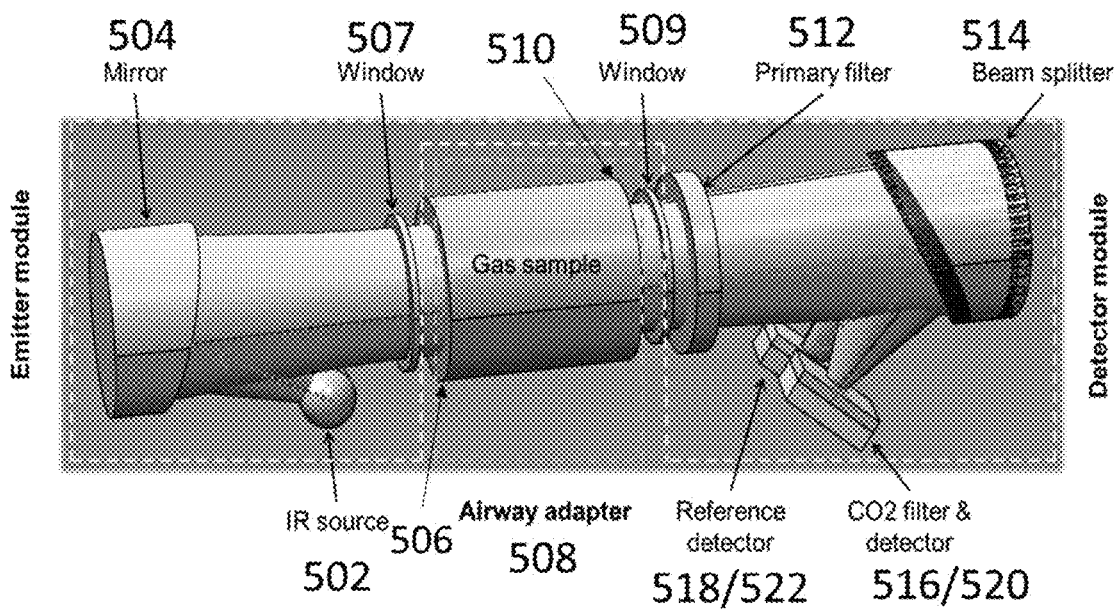
FIG. 5B illustrates a perspective view of the arrangement of optical components and the light rays propagating in the system (calculated by ray tracing analysis), for an embodiment of the mainstream solid-state gas spectrometer in accordance with certain aspects of the present disclosure.

In the example shown in FIG. 5A, the focusing beam splitter is a segmented concave mirror 514 that transforms the light beam received from the second device window 509, into two focused reflected beams. One of the focused beams, illuminates a sensing detector 520 via a sensing filter 516 (disposed on the sensing detector 520) and the other focused beam illuminates a reference detector 522 via a reference filter 518 (disposed on the reference detector 522). In some examples, the sensing 520 and reference 522 detectors may be positioned side-by-side in front of the reflective surface of the segmented concave mirror 514 below the axis of the incident light beam. In some examples, the illuminated area on each detector may be smaller than the area of the sensitive area of the detector and has a shape that can be fully contained in the sensitive area of the detector (e.g., square, circle and the like). In some such examples, the illuminated area on each detector can be an anamorphic image of the light emitting region or element of the emitter 502. Further details about the segmented concave mirror and other devices that may serve as a focusing beam splitter are discussed below. FIG. 5B illustrates a perspective view of the propagation of a bundle of rays generated by the light emitter 502 through the spectrometer arrangement shown in FIG. 5A.

Figure 6:
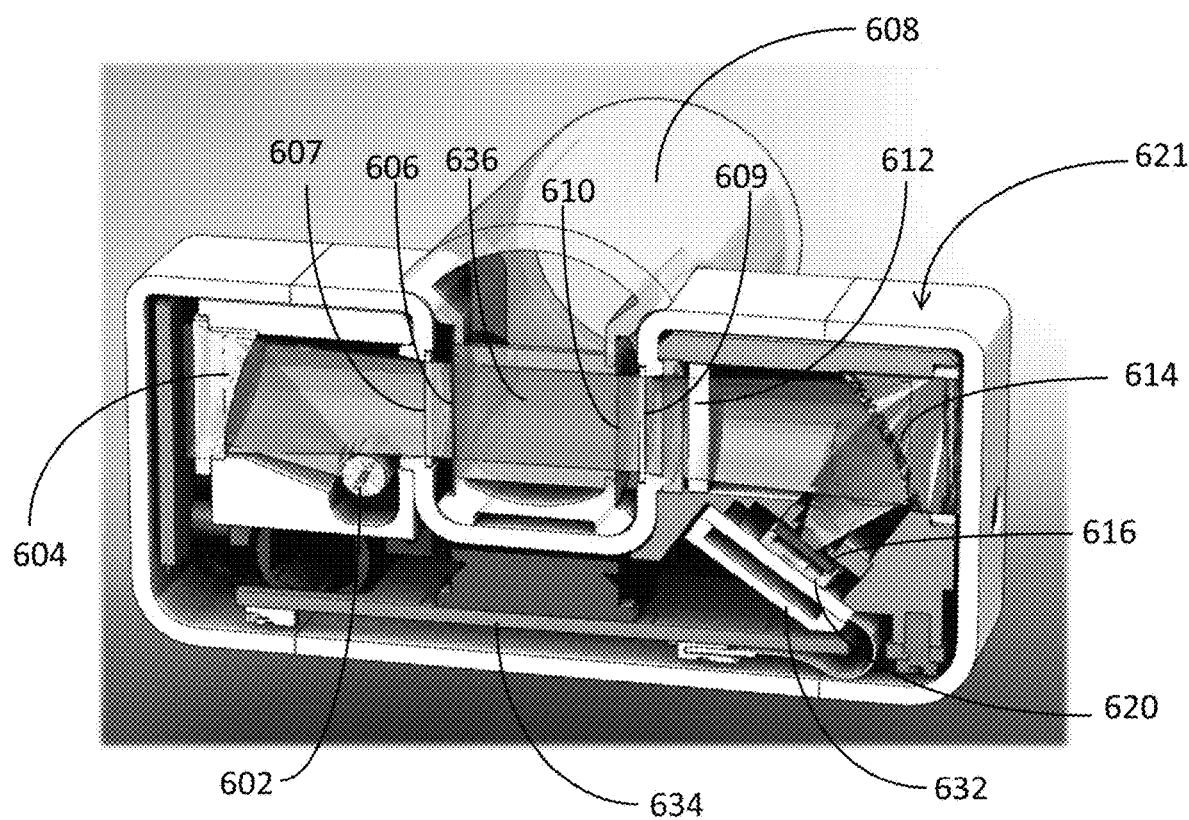
FIG. 6 illustrates a cross-sectional perspective view of the mainstream solid-state gas spectrometer enclosed in a housing in accordance with certain aspects of the present disclosure.

FIG. 6 illustrates a cross-sectional perspective view of an example of the mainstream solid-state gas spectrometer based on the optical arrangement shown in FIGS. 5A and 5B. In this example, the optical components are placed in an enclosure 621 that may be integrated with the airway adapter 608 of the spectrometer. In some examples, the airway adapter 608 may be a separate component (e.g., a removable and disposable component) and can be detached from the enclosure 621. In some such examples, the enclosure 621 includes two device windows 607/609 that isolate and protect the components inside the enclosure 621 (e.g., when the airway adapter 608 is removed). The side walls of the airway adapter 618, may include two windows, an entrance window 606 facing the emitter 604 and an exit window 610 facing the beam splitter 614. The apertures and therefore the entrance 606 and exit 610 windows, are positioned and optically aligned on opposite faces of the airway to provide a clear path for transmission of the collimated beam 636 through the airway adapter 608. As mentioned above, one or both sides of the entrance window 606, exit windows 610, the first device window 607 and the second device window 609 may be coated with an antireflection (AR) coating layer. In some examples, each one of these windows 606/607/609/610 can be a sapphire window.

A circuit board 634 may be also included in the enclosure 621. This circuit board may include the signal processing module 232 and other analog and digital electronic circuitry needed for controlling the light source, signal acquisition from the detectors, signal processing and controlling a user interface (e.g. a display and a keypad or a touchscreen display) that may be used to receive user inputs and display the results (e.g., concertation of one or more target gas molecules). In some examples, the signal processing module 232 may include a non-transitory memory and a hardware processor that may execute instructions stored in the non-transitory memory. The internal volume of the enclosure 621 may be structured to facilitate the placement and alignment of the emitter 602, the collimating mirror 604, a primary filter 612, the focusing beam splitting mirror 614, the sensing detector 620 (covered by the sensing filter 216), and the reference detector. For example, a seat with aligning marks may be provided for each one these components so that solid-state mainstream spectrometer can be assembled by placing each component in the designated seat. In some such examples, the internal structure of the enclosure 621 and the seats may be fabricated with a precision that eliminates the need for further alignments after placing each component.

In certain embodiments, the emitter 602 can be a thermal IR emitter (e.g., a coiled wire emitter or a thin film emitter enclosed in a sealed enclosure). In some other examples, the emitter 602 can be an IR light emitting diode (LED) or other light sources based on semiconducting materials and junctions (e.g., quantum dot emitters, semiconductor lasers and the like). In yet other examples, the emitter 602 can be a laser emitter (e.g., a mid-IR laser such as a quantum-cascade (QCL) laser). Each one of these emitters may have different form factors and emit light beams with different cross-sessional profiles and divergences. The segmented concave mirror 614 may be designed according to the cross-sectional profile of the light emitted by the selected emitter such that an anamorphic image of the emitter can be formed on the sensitive area of each one the detectors.

The concave mirror 604 can be a parabolic mirror (e.g., an off-axis parabolic mirror). The concave mirror 604 may be a metallic mirror or a mirror formed by coating a substrate (e.g., an injected molded plastic substrate) with one or more layers (e.g., a metallic layer or multiple dielectric layers). In some examples, the substrate can be fabricated using injection molding. The concave mirror 604 can be highly reflective for the all or a subset of wavelengths emitted by the emitter 602. For example, the reflectivity the concave mirror 604 can be larger than 50%, 60%, 80% or 90% for light having wavelength within a certain wavelength range (e.g., between 2000 nm and 5000 nm, 5000 nm and 8000 nm or 8000 nm and 12000 nm).

The entrance window 606, the exit window 610, the first device window 607 and the second device window, may have different shapes (e.g., circular, rectangular, elliptical and the like). The thickness of each window may be between 0.1 mm to 1 mm or 1 to 2 mm. The diameter each windows 606/607/609/610 can be between 1 mm and 10 mm or mm and 15 mm. In some examples, other designs may be adopted for the entrance and exit windows (e.g., the design disclosed in U.S. Pat. No. 7,629,039 B2). The windows 606/607/609/610 may be formed from materials that are transparent at least in a portion of the emission spectrum of the emitter (e.g., has a luminous transmittance of greater than 70%, 80% or 90% in said portion). In certain embodiments, the windows may be transparent in the wavelength range associated with one or more absorption lines of the target molecules and another wavelengths range that do not overlap with any of the absorption lines of the target molecules. For example, for detection of target molecules based on their absorption band in near and mid-IR region, the windows may be formed from silicon, sapphire, silicon, ZnSe, ZnS, LiNbO3, fluoride base glasses (e.g., $BaF_2$, $CaF_2$), Potassium bromide (KBr), chalcogenide materials (e.g., Schott IRG) and the like. The windows 606/607/609/610 may be coated by antireflection layers to reduce reflections within the bandwidth if the emitted light by the emitter 602. The entrance 606 and exit 610 windows may have identical or different shapes and thickness. The first 607 and second 609 device windows may have identical or different shapes and thickness.

In some embodiments, the sensing detector 620 and the reference detectors can be of thermopile type (e.g., tungsten wire lamp in a vacuum housing). Advantageously, using a thermal source may improve the power efficiency of the system while reducing the cost. In some other examples, the sensing and the reference detectors may be cooled or uncooled semiconductor photodiodes. In yet other examples, the sensing and the reference detectors may be any detector that can convert light having a wavelength within a wavelength interval between 1000 nm-12000 nm to an electric signal.

In certain examples, the sensing detector 620 and the reference detector can be of the same type and have identical responses (e.g., identical spectral responses and/or identical optical-to-electrical conversion efficiency). In some other examples, each detector may have an optimal response within pass band of the filter covering that detector. The sensitive areas of the detectors may be between 0.01 $mm^2$ and 5 $mm^2$, or 5 $mm^2$ and 10 $mm^2$.

The sensing filter 616 and the reference filter can be stand-alone multilayer dielectric filters formed by coating one or more dielectric layers on a transparent substrate. The filters may have different shapes and their area can be between 1 $mm^2$ and 25 $mm^2$.

In some examples, instead of using stand-alone filters, a multilayer dielectric filter may be formed on the sensitive surface of the sensing and reference detectors using various methods (e.g., e-beam coating, sputtering, evaporation coating, MOCVD, MBE and the like).

Beam Splitter Design

In some examples of the disclosed mainstream gas spectrometer (e.g., those shown in FIG. 5 and FIG. 6), the focusing beam splitter 514 (or 614) can be a single reflective element designed to transform an incident light beam (e.g., the collimated beam 536/636 transmitted through the airway adapter 508/608) into two reflected focused beams with minimal radiative (optical) power loss. In some such examples, the incident light beam may be a collimated beam. In some other examples, the reflective focusing beam splitter may be designed to transform an incident light beam with an arbitrary divergence and profile into two reflected focused beams. The profile (or rate of convergence) and direction of each one of the resulting focused beams are determined by the design of the reflector. The ratio between the magnitudes of the power transferred to each one of the two focused beams (i.e., the splitting ratio), that is also determined by the design of the reflector, may be 50/50, 60/40, 20/80, 10/90 or other ratios.

Figure 7A:
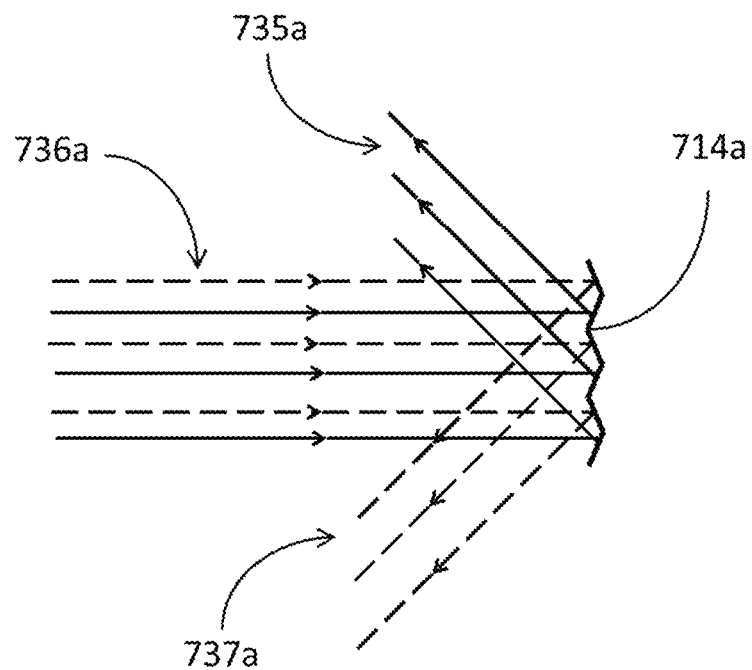
FIG. 7A is a schematic diagram illustrating parallel incident rays divided by a two-dimensional flat segmented reflector with triangularly shaped surface.

An example of a reflective beam splitter is a segmented reflecting surface or a segmented mirror. FIG. 7 illustrates the working principle of a segmented reflecting surface in the context of two dimensional (2D) segmented reflectors. In the example shown in FIG. 7A, the reflecting surface of the 2D reflector 714a has a periodic cross-section (e.g., sawtooth shaped cross-section) wherein each period is shaped as an isosceles triangle with a vertex angle that is larger than 0 degree and less than 180 degrees. Since the apexes of these triangles form a straight line, the reflector in this example is a flat segmented reflector. As evident from the trajectory of light rays shown in FIG. 7A, a flat segmented mirror may divide a bundle of parallel light rays 736a into two bundles of reflected light 735a/737a rays wherein the rays within each bundle are also parallel to each other. The splitting mechanism can be understood by noticing that reflecting facets can be divided into two groups each comprising to reflecting facets that are parallel to each other and therefore reflect the incident rays in the same direction. Since in this example all facets have the same area and the number of facets in the two groups are equal, half of the rays are reflected by the facets in one group and the other half are reflected by the facets in the other group effectively generating two reflected bundle of rays 735a/737a each carrying half of the power provided by the incident bundle of rays 736a.

Figure 7B:
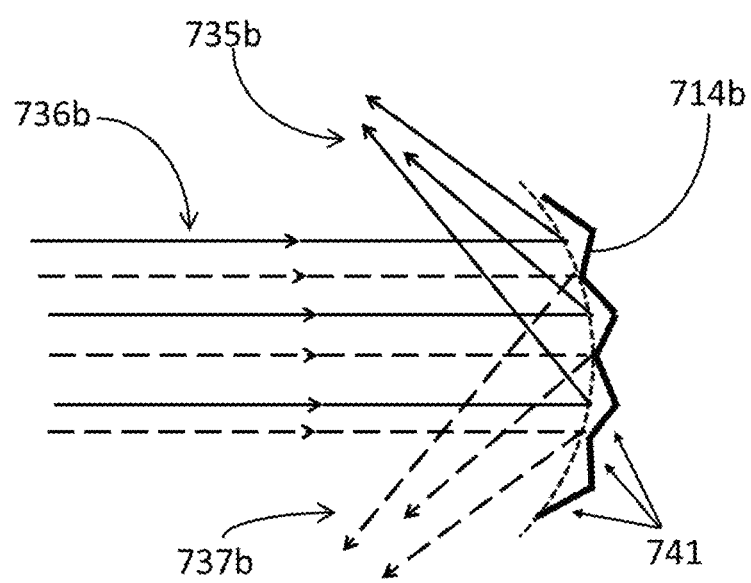
FIG. 7B is a schematic diagram illustrating parallel incident rays divided by a two-dimensional concave segmented reflector.

In some cases, the apexes of the cross-sectional triangles of a 2D segmented reflector form a curved line (e.g., a curved line having a parabolic shape or elliptical shape). In such cases, the reflector is a curved segmented reflector. A curved segmented mirror with a concave reflecting surface may be used to simultaneously divide an incident beam of light and focus the resulting light beams. The example shown in FIG. 7B is a 2D concave segmented reflector 714h. As evident from the trajectory of light rays shown in FIG. 7B, a concave segmented reflector 714h may divide a bundle of parallel light rays 736b into two bundles of reflected light rays 735b/737b wherein the rays within each bundle are convergent. In some examples, each segment 741 can be also a curved surface. Advantageously, curved segments may form beams with smaller spot size at the focal point (e.g., on the surface of the sensing or reference detector). The principle described above, can be implemented for designing and fabricating three dimensional (3D) concave segmented reflectors capable of transforming an incident collimated light beam with a given cross-sectional shape and area into two focused light beams in three dimensional space. More specifically, the reflecting surface can be divided into a plurality of segments 741 wherein each segment may have a flat surface or curved surface oriented to reflect right in a specific direction. With careful design, the plurality of segments can divide the entire cross-section of an incident beam into two convergent beams with desired degree of convergence and propagating along specific directions.

Figure 8A:
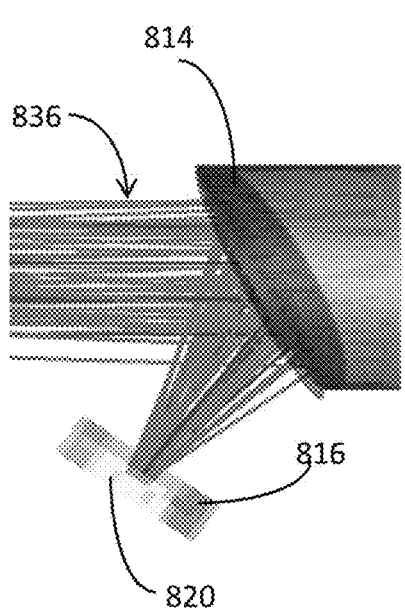
FIG. 8A illustrates a side view of a concave segmented reflector transforming a collimated beam into two focused beams.
Figure 8B:
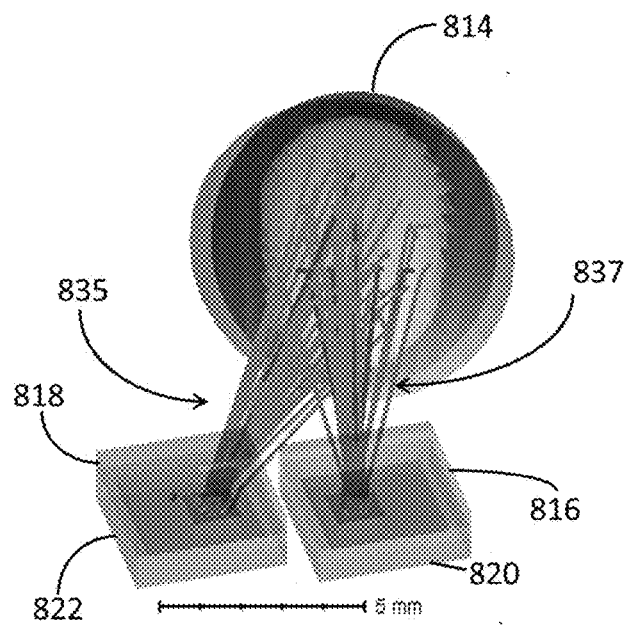
FIG. 8B illustrates a front perspective view of two focused beams generated by the curved segmented reflector shown in FIG. 8A, each beam focused on a detector covered by a filter.

FIGS. 8A and 8B illustrate a side view and perspective view of a concave segmented reflector 814, illuminated by a collimated beam of light 836, respectively. As evident from the trajectory of light rays, the concave segmented mirror 814 divides the collimated incident light beam 836 into two reflected and focused light beams 835/837. As such, the concave segmented reflector 814 may function as a focusing beam splitter in the disclosed configurations of a gas spectrometer (e.g., those shown in FIG. 5 and FIG. 6). As shown in FIG. 8B, the concave segmented reflector 814 may be designed to generate a first light beam 835, by dividing the incident light beam (e.g., a collimated light beam), focused on the reference filter 818 disposed on the reference detector 822, and a second light beam 837, focused on the sensing filter 816 disposed on the sensing detector 820. In some examples, the focal points of the resulting reflected beams 835/837 may be positioned on or near the reference 822 and sensing 820 detectors. Advantageously, the segmented reflector 814 can be designed to focus these beams on closely spaced detectors (e.g., two detectors mounted side-by-side on printed circuit board).

In some embodiments, the concave segmented mirror 814 may transform an incident beam of light (e.g., the collimated beam of light 836) into a first convergent beam 837 and a second convergent beam 835. In some such embodiments, the concave segmented mirror comprises two groups of reflecting surfaces where a first group of reflecting surfaces transform a first portion of the incident beam into the first convergent beam 837 and the second group of reflecting surfaces transform a second portion of the incident beam into the second convergent beam 835. In some cases, the power (e.g., an optical power) carried by the first portion of the incident beam may be substantially equal to the power carried by the second portion of the incident beam. In some cases, a difference between the power (e.g., an optical power) carried by the first portion of the incident beam and the power carried by the second portion of the incident beam, may be less than 5%, 10% or 20% of the total power carried by the incident beam. The first and the second convergent beams 837/835 may propagate along two different directions and may converge toward two different points or two different areas. For example, the first convergent beam 837 may propagate and converge toward an area on the sensing detector 820, and the second convergent beam 835 may propagate and converge toward an area on the reference detector 822.

A reflecting surface of a group of reflecting surfaces (e.g., the first or the second group), may have a parabolic shape, a near parabolic shape or other shapes that may transform a bundle of parallel light rays to a bundle of convergent light rays. In some cases, a shape of a reflecting surface in a group of reflecting surfaces (e.g., first or second group), may be selected such that the bundle of convergent light rays generated by the reflecting surface, converges toward the same convergence areas or convergence point where the bundle of convergent light rays generated by another reflecting surface in the group converge.

In some cases, the concave segmented mirror 814 may comprise a plurality grooves (e.g., of V-shaped grooves) where each surface of a groove is a reflecting surface of a different group of reflecting surfaces. A two-dimensional cross-section of such concave segmented mirror may have a sawtooth shape corresponding to cross-sections of the plurality of V-grooves. In some cases, the apexes of the V-grooves may be form a curved line (e.g., a curved line having a parabolic or elliptical shape)

Figure 8C:
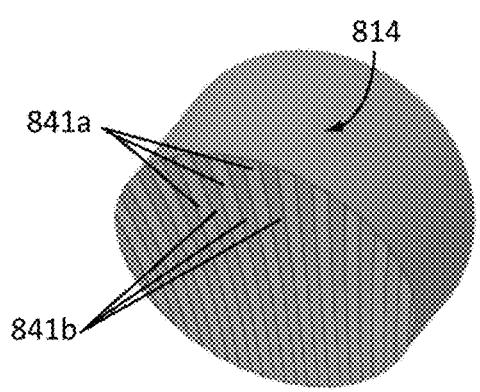
FIG. 8C illustrates a three dimensional perspective view of an example concave segmented mirror comprising two sets of elliptic parabolic reflecting surfaces.
Figure 8D:
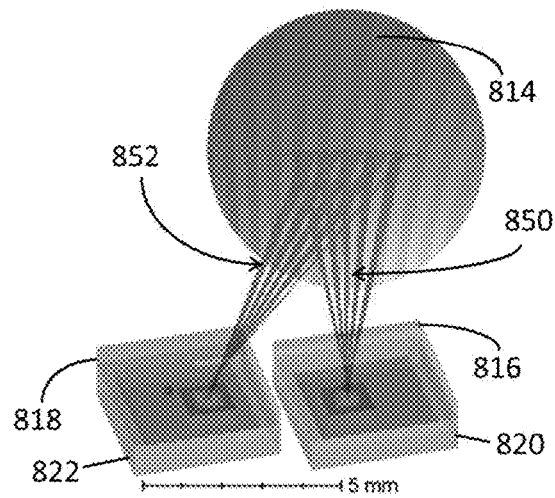
FIG. 8D illustrates, an example wherein a concave segmented mirror comprising two sets of elliptic paraboloids splits and focuses an incident beam of light on the reference and sensing detectors.

In some examples, the concave segmented mirror may comprise two sets (or groups) of elliptic paraboloids (e.g., an elliptic paraboloid may have parabolic vertical cross sections and elliptical horizontal cross sections). Each set of elliptic paraboloids may include a plurality of parabolic or elliptic parabolic reflecting surfaces that focus an incident beam (e.g., a collimated incident beam) on either the reference detector or the sensing detector. In some such examples, the two sets of paraboloids are interlaced. FIG. 8C shows a three dimensional perspective view of an example concave segmented mirror 814 with two sets 841a/841b of elliptic paraboloids. In some examples, the segments in each set of paraboloids 841a/841b can be sawtooth shaped grooves. The period of the sawtooth grooves may be between 0.1-1 mm, 1-2 mm, 2-5 mm or other values. FIG. 8D illustrates, an example wherein a concave segmented mirror comprising two sets of elliptic paraboloids (e.g., the concave segmented mirror shown in part-C) focuses portion of an incident beam on each detector. As shown in the figure, the light rays 850 reflected by a first set of elliptic paraboloids are focused on the sensing 816 filter placed on the sensing detector 820, and the light rays 852 reflected by a second set of elliptic paraboloids are focused on the reference 818 filter placed on the reference detector 822.

In some embodiments, a segmented reflector (e.g., a segmented reflector with elliptic paraboloids) may generate three or more reflected light beams (e.g., convergent light beams). For example, the reflecting segments (or surfaces) may include three or more groups of reflecting surfaces. Each group of reflecting surfaces may be designed and arranged to reflect a portion of a received light beam (e.g., from the light emitter 202) to a different direction. In some cases, each group of reflecting surfaces may be designed and arranged to reflect and focus a portion of the received light beam on a light detector of a plurality of light detectors. In some cases, the segmented reflector may generate three or more reflected light beams having equal intensities and/or carrying the same amount of optical power. In some cases, the segmented reflector may generate three or more reflected light beams that carry different amounts of power (e.g., optical power) where differences among the amounts of power carried by different reflected beams is less than 5%, 10%, or 20%. In various embodiments, segmented reflectors that generate three or more reflected light beams upon illumination by an incident beam of light (e.g., a collimated beam of light), may focus the reflected light beams on three or more light detectors. In some cases, one of the three or more detectors may be a reference detector and each or the remaining detectors may be a sensing detector. In such cases, each sensing detector may be covered by a sensing filter associated with one or more absorption wavelength bands of a target molecule. The sensing signal generated by each sensing detector and the reference signal generated by the reference detector may be used (e.g., by the signal processing module 232) to simultaneously measure the concentration of a plurality of target molecules.

The effective bandwidth and the central wavelength of a filter (e.g., the sensing filter 816 or the reference filter 818) may change with the angle of incidence on the filter (e.g., the angle at which the beam is incident on the surface of the filter). As such, only the portion of a beam that is incident on the filter with an angle of incidence within certain range, may be filtered according to designed filter function (i.e., the transmission spectrum of the filter characterized by its center wavelength and bandwidth). In some examples, the filter may support a specific filter function only if the angle of incidence is less than 10, degrees, or 20 degrees, or 30 degrees. Advantageously, the reflective beam splitter 814 described above, can generate beams 835/837 with certain divergence or angular frequency content (i.e., the range of angles between rays forming the beam and the direction of the propagation), so that a large portion of the optical power carried by each beam (e.g., larger than 90%, larger than 70%, larger than 50%) is filtered according to designed transmission spectrum of the corresponding filter (e.g., the sensing filter 818 or the reference filter 816).

In some examples, the collimating mirror 604 and the curved segmented reflector 814 may collectively function as an anamorphic imaging system wherein an anamorphic image of the light emitting element of the light emitter is formed on each detector. The said anamorphic image of the light emitting element formed on each detector 820/822, may be fully contained in the sensitive region of each detector 820/822. In some other examples, the area of the illuminated region on each detector may be smaller than the sensitive area of the detector by a margin than is larger than the uncertainty associated with the placement of the detector on a detector seat provided inside the housing 621.

Figure 9A:
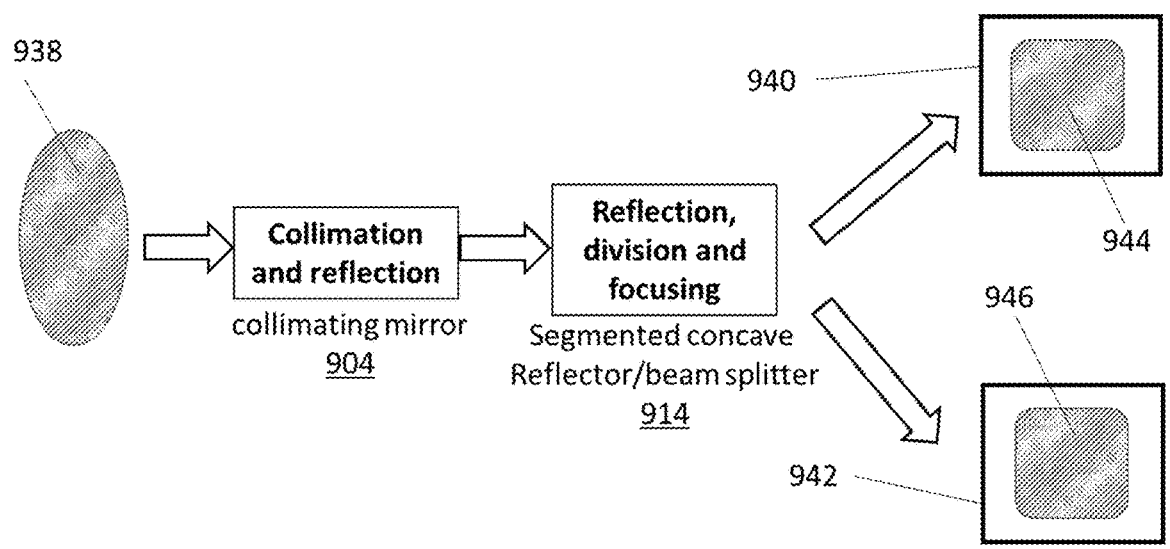
FIG. 9A illustrates the projection of the light beam with an elongated profile (e.g., generated by a thermal emitter) on two square shaped regions on the sensitive areas of two light detectors.

FIG. 9A illustrates an example of such anamorphic projection wherein the light generated by a thermal emitter, is projected on the sensitive areas of the sensing 940 and reference 942 detectors. In this example, the divergent beam of light emitted by the light emitting element of the light emitter (e.g., a filament, a ribbon and the like) has an elongate profile 938. The emitted light is first reflected and collimated by the collimating mirror 904. After passing through the airway adapter 508, the transmitted beam of light is projected by the concave segmented reflector 914 (e.g., the concave segmented reflector 814 in FIGS. 8B, 8C and 8D) on two square shaped regions 944/946; one on the sensitive area 940 of the sensing detector and the other on the sensitive area 944 of the reference detector.

Figure 9B:
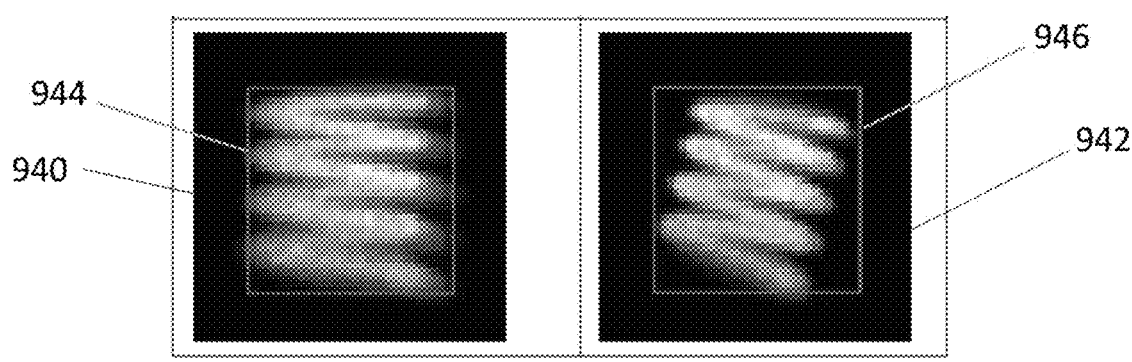
FIG. 9B illustrates the images of the emitting element of a thermal light emitter on the sensing and reference detectors formed by a reflective beam splitter.

FIG. 9B illustrates an example of anamorphic projection wherein the image of the emitting element (e.g., a coil) of a thermal light emitter is projected on two square shaped regions 944/946; one on the sensitive area 940 of the sensing detector and the other on the sensitive area 944 of the reference detector.

The curved segmented reflector 814 described above may be formed from low cost materials and using low cost manufacturing techniques. For example the curved segmented reflector may be formed by injection molding of plastic materials and coating the reflecting facets with a highly reflective layer (e.g., a gold layer).

Advantageously, if the segmented reflector is formed by injection molding, the reflector may be monolithically integrated with a larger part designed to be placed in the housing 621 of the spectrometer. The said part may facilitate the optical alignment of the reflector 814 (614 in FIG. 6) with respect to the airway adapter window 610 and/or the sensing/reference detectors 820/822.

Alternative Beam Splitter Designs

Figure 10A:
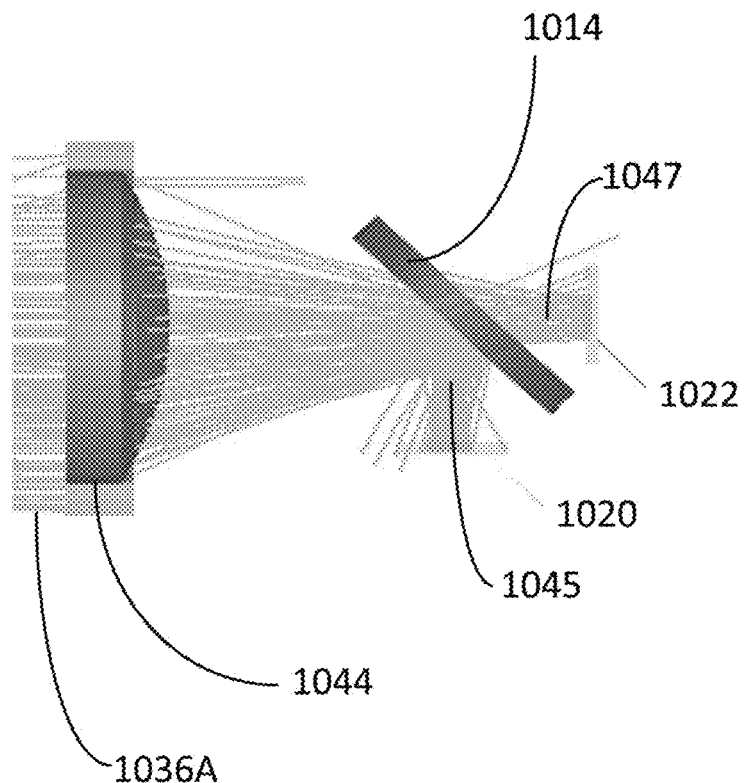
FIG. 10A illustrates the transformation of a collimated beam to a transmitted focused beam and a reflected focused beam by a plano-convex lens and a partially transmissive beam splitter.

In some embodiments, the single element focusing beam splitter may be replaced by two separate elements. In these embodiments a focusing element may be used to focus the collimated beam of light (transmitted through the gas stream) and a non-focusing (flat) beam splitter, placed in a location between the focusing element and the waist of the focused beam, may be used to divide the incident focused beam into two focused beams each illuminating one of the detectors. The focusing element can be a lens that transforms the collimated beam of light (e.g., the beam of light generated by the emitter 202 and received from the gas adapter 208) into a convergent beam of light. In some examples, the focusing element can be a positive lens and the splitting element can be a dielectric slab. An example of a two-element beam focusing and splitting stage is illustrated in FIG. 10A. In this example, a collimated beam of light 1036A is first focused by a plano-convex lens 1044 (the focusing element) and the focused beam of light is partially reflected by a dielectric slab 1014 (splitting element). So effectively the lens 1044 and the slab 1014 transform the collimated beam 1036A into two focused (or convergent) beams. The first focused beam 1047 is transmitted through the slab 1014 and illuminates, for example, the reference detector 1022, and the second beam 1045 is reflected by the slab 1014 and illuminates, for example, the sensing detector 1020.

The positive lens can be designed to transform a collimated incident beam of light with a given diameter to a focused beam. A dielectric slab having two parallel surfaces, and no additional coating layer, can act as a partially transmitting beam splitter wherein the light incident on the first and the second surfaces of the slab are partially reflected and partially transmitted according to the Fresnel coefficients associated with the air-dielectric interfaces at both sides of the slab. As such, the ratio between the power of the transmitted beam and the power of the reflected beam (i.e., power splitting ratio) and wavelength dependence of the splitting ratio are determined by the thickness of the slab and the material from which the slab is made of.

In configurations where separate focusing and beam splitting elements are used, the filters (that tailor the light spectrum for the sensing and references detectors), may be placed in the vicinity of reflecting and transmitting surfaces of the beam splitter. Such an arrangement may increase the tolerance for misplacing the detectors with respect to the transmitted and reflected beams.

In some examples, one or more dielectric layer may be deposited on one of the surfaces of the slab to provide a tailored spectral response and splitting ratio. In some such examples, light having wavelengths within a first wavelength range may be reflected and light having wavelengths within a second wavelength range may be transmitted. The ratio between the power of the transmitted light and the power of the reflected light can be controlled by the number of layers, refractive index and the thickness of each layer of the multilayer coating. For example, the number of layers, their composition and their thickness can be selected such that the slab transmits light with wavelength within one or more absorption wavelength bands of the target molecule and reflects all other wavelengths or reflects wavelength in another wavelength band not overlapping with any of the absorption wavelength bands of the target molecule. In some other examples, one side of the dielectric slab may be coated with a thin reflecting layer (e.g., a metallic layer such as gold, silver and the like). Such layer may function as a broadband partial reflector with a splitting ratio determined by the thickness of the metal coating.

For an NDIR spectrometer, the lens and the dielectric slab may be formed from materials that are transparent a cross a spectral range within IR region (e.g., silicon, sapphire, silicon, ZnSe, ZnS, LiNbO$_3$, fluoride base glasses and the like). The lens and the slab can be made of the same or different materials. For example, the lens can be made from sapphire while the slab may be made of silicon.

Figures 10B, 10C:
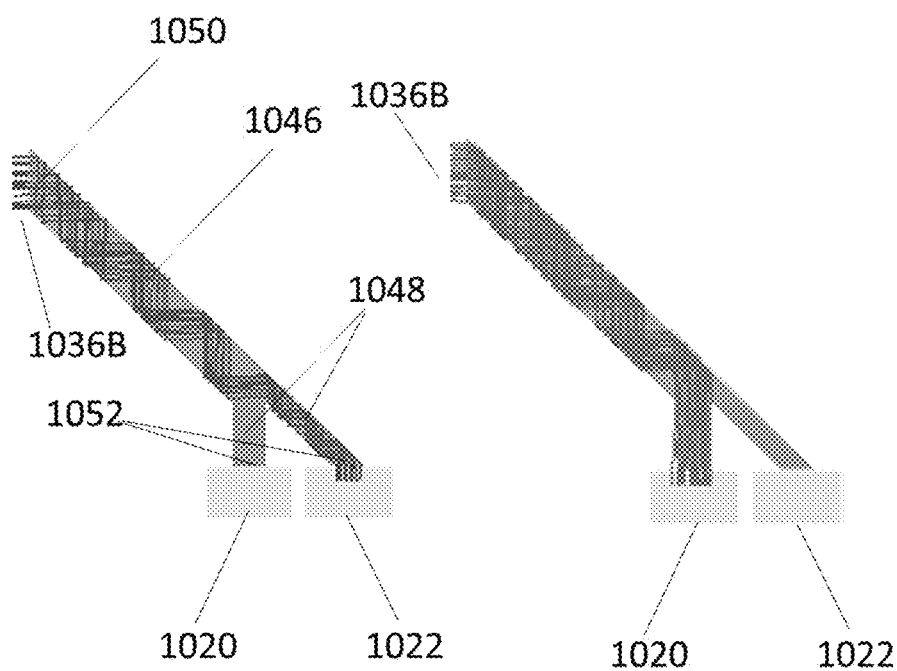
FIGS. 10B and 10C illustrate beam splitting by a forked light guide. Part-B: illustrates a subset of light rays exiting the output segment that illuminates the reference detector. Part-C: illustrates a subset of light rays exiting the output segment that illuminates the sensing detector.

In some embodiments, the single element focusing beam splitter may be replaced by a guided wave splitter comprising an input waveguide segment connected to two output waveguide segments wherein a portion of the radiative power coupled to the input waveguide segment is output from one of the output waveguide segments and the rest is output form the other output waveguide segments. The ratio between the portions coupled to each output segment may is determined by the geometry of the guided wave splitter and therefore selectable by design. An example of such guided wave splitter is the forked lightguide shown in FIGS. 10B and 10C. The forked lightguide can include an input section 1046 that is forked into two output segments 1048, one for illuminating each detector 1020/1022. The collimated beam 1036B (transmitted through the airway adapter), enters the input waveguide section 1046 via an entrance port 1050. The light rays entering the input waveguide section 1046 may enter one of the output segments 1052 depending on their point of entree in the entrance port 1050 of the input waveguide 1046. The exit ports 1052 of the output waveguide segments can be aligned with the respect to the sensing detector 1020 and the reference detector 1022 such that the light provided by each output waveguide section only illuminates one of the detectors (i.e., the reference or the sensing detector). For example, a subset of light rays in the collimated beam 1036B, shown in FIG. 10B, exit the output segment that illuminates the reference detector 1022, while another subset of light rays in the collimated beam 1036B, shown in 10C exit the output segment that illuminates the sensing detector 1020.

The guided wave splitter may be designed to only illuminate the sensitive areas of the sensing and reference detectors with minimum radiative power loss from the collimated light beam, transmitted through the airway adapter, to the detectors. In some examples, wherein the waveguides are made of a dielectric material, the light may travel and stay confined inside each one of the waveguide segments by total internal reflection (TIR) without the need for any coating on the waveguides. In some other embodiments, the waveguides may be formed as hollow structures. In these embodiments, the internal surface of the waveguides may be coated with a material that can efficiently reflect the light emitted by the light emitter (e.g., metals such as gold, silver, copper, . . . ). In other embodiments, the hollow waveguides may be formed from metallic materials that naturally reflects light emitted by the light emitter.

Such forked lightguide can be made as a hollow structure wherein the internal surface of the walls are gold coated to provide high reflection for light with wavelengths within IR spectral range. The geometry of the forked lightguide may be tailored to support a desired splitting ratio and optimal power transfer efficiency to the detectors (i.e., minimal power loss). The cross-section of the output segments may be designed to illuminate a region on the detector having an area smaller than the sensitive area of the detector and a shape that can be fully contained within the sensitive area of the detector ide carefully, the splitting and efficiency can be optimized.

Beyond their medical applications discussed above, the solid-state gas spectrometers disclosed herein may be used to measure the concentration of carbon dioxide for variety of non-medical applications.

Solid-state gas spectrometers may be used in industrial facilities to monitor air quality conditions to ensure $CO_2$ level remain within a set limit.

Measuring $CO_2$ concentration plays an important role in various stages of food processing & food storage industry. For example, many food items are packaged using modified atmospheric packaging (MAP) technique to help improve the shelf life of fresh or minimally processed foods. MAP may require modifying the composition of the internal atmosphere of food packages to decelerate the natural deterioration of the food product. $CO_2$ is one of the most significant gases used in modified atmosphere packaging and storage to inhibit the growth of microorganisms responsible for spoilage. As such, fast and accurate measurement of $CO_2$ concentration in the internal atmosphere of a package using a sample volume is critical for MAP. The small form factor, fast response time, and small volume of the gas sample required for $CO_2$ measurement makes the solid-gas spectrometers described above as excellent candidate for monitoring $CO_2$ level inside a food package to make sure the concentration is within a set range required for optimal shelf life.

In may agricultural industries, maintaining a controlled environment with a set level of $CO_2$ level is important to promote plant growth and reduce the risk of contamination, degradation, and infestation of picked produced. The compact size, fast response time of the solid-gas spectrometers described above may enable them to ensure $CO_2$ remains at the desired levels in the controlled environment.

Combustion plays an important role in various industrial equipment and systems, such as boilers, furnaces, and heaters, and the like. In these industries $CO_2$ sensors, such as those described above, can be used to determine system performance and efficiency, by monitoring $CO_2$ level in a flow of gas provided to a combustion chamber.

In some applications, the solid-state gas spectrometers described above may be used to simultaneously measure the concentration of two or more gas molecules, for example, using at least one segmented reflector that generates three or more reflected light beams directed to three or more light detectors. For example, in the context of MAP described above, the solid-state gas spectrometers may be used to simultaneously measure the concentration of two or more gases (e.g., $CO_2$, Nitrogen and Oxygen) inside a food package to make sure the concentration of each molecule is within a set range required for optimal shelf life. Similarly, the disclosed solid-state gas spectrometers may be used to simultaneously monitor the concentration of two or more gases in an environment (public places, agricultural facilities, barns, and the like), in a gas line (e.g., gas line feeding a combustion chamber), and the like.

Terminology

Although these inventions have been disclosed in the context of certain embodiments and examples, it will be understood by those skilled in the art that the present inventions extend beyond the specifically disclosed embodiments to other alternative embodiments and/or uses of the inventions and obvious modifications and equivalents thereof. In addition, while several variations of the inventions have been shown and described in detail, other modifications, which are within the scope of these inventions, will be readily apparent to those of skill in the art based upon this disclosure. Furthermore, various applications of such embodiments and modifications thereto, which may occur to those who are skilled in the art, are also encompassed by the general concepts described herein. Optional features of various device and system embodiments may be included in some embodiments and not in others. The foregoing description is provided primarily for exemplary purposes and setting forth specific details of various embodiments; therefore it should not should not be interpreted to limit the scope of the invention as it is set forth in the claims.

It should be understood that various features and aspects of the disclosed embodiments can be combined with or substituted for one another in order to form varying modes of the disclosed inventions. Each and every feature described herein, and each and every combination of two or more of such features, is included within the scope of the present invention provided that the features included in such a combination are not mutually inconsistent.

The limitations in the claims are to be interpreted broadly based on the language employed in the claims and not limited to the examples described in the present specification or during the prosecution of the application, which examples are to be construed as non-exclusive.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether.

While the above detailed description has shown, described, and pointed out novel features as applied to various examples, it will be understood that various omissions, substitutions, and changes in the form and details of the devices illustrated can be made without departing from the spirit of the disclosure. As will be recognized, the inventions described herein can be embodied within a form that does not provide all of the features and benefits set forth herein, as some features can be used or practiced separately from others.

For purposes of this disclosure, certain aspects, advantages, and novel features are described herein. It is to be understood that not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language used herein, such as, among others, "can," "might," "may," "for example," and the like, unless specifically stated otherwise, or otherwise understood within the context as used, is generally intended to convey that certain examples include, while other examples do not include, certain features, elements and/or states. Thus, such conditional language is not generally intended to imply that features, elements and/or states are in any way required for one or more examples or that one or more examples necessarily include logic for deciding, with or without author input or prompting, whether these features, elements and/or states are included or are to be performed in any particular example. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Disjunctive language such as the phrase "at least one of X, Y, or Z," unless specifically stated otherwise, is otherwise understood with the context as used in general to present that an item, term, etc., may be either X, Y, or Z, or any combination thereof (for example, X, Y, and/or Z). Thus, such disjunctive language is not generally intended to, and should not, imply that certain examples require at least one of X, at least one of Y, or at least one of Z to each be present.

All figures, tables, and appendices, as well as patents, applications, and publications, referred to above, are hereby incorporated by reference. Additionally, all publications, patents, and patent applications mentioned in this specification are herein incorporated by reference to the same extent as if each individual publication, patent, or patent application was specifically and individually indicated to be incorporated by reference.

Some embodiments have been described in connection with the accompanying drawing. However, it should be understood that the figures are not drawn to scale. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

In this description, references to "an embodiment," "one embodiment," or the like, mean that the particular feature, function, structure or characteristic being described is included in at least one embodiment of the technique introduced herein. Occurrences of such phrases in this specification do not necessarily all refer to the same embodiment. On the other hand, the embodiments referred to are also not necessarily mutually exclusive.

In some cases, "infrared (IR) wavelength ranges" may be divided into three ranges termed near-IR, mid-IR, and far-IR wavelength ranges. In some cases, an IR or an NDIR gas sensor or spectrometer may correspond to a gas sensor or spectrometer that determines the concentration of a target gas molecule in a gas sample based on absorption wavelength bands of the target molecule in one or more IR wavelength ranges. Further, it should be understood that IR wavelength ranges may include additional ranges, such as short-wavelength infrared and long-wavelength infrared. Generally, although not necessarily, the infrared range of between 1.5-6 microns may be used for gas sensing. In addition to its plain meaning, "light" may refer to electromagnetic radiation having a wavelength between, for example, 0.4 to 15 microns spanning visible (0.4 to 0.75 microns), near-IR (0.75 microns to 1.5 microns), mid-IR (1.5 microns to 8 microns) and far-IR (larger than 8 microns) wavelength ranges.

Several terms are used interchangeably within this description. Each of the terms are intended to have their customary ordinarily understood plain meaning in addition to the meanings described throughout this application. For example, the terms "electromagnetic power", and "optical power" can be used interchangeably. In addition to their plain meanings, the foregoing terms may refer to amount of electromagnetic energy delivered per unit time (i.e., each second). It should be also understood that "wavelength band" and "frequency band" can be used interchangeably as they both refer to a limited spectral range in a broad spectrum. It should be further understood that "detector", "light detector" and "photodetector" can be used interchangeably, all referring to a device that generates an electric signal (e.g., current or voltage) proportional to the power of the optical power received by the device.

For clarity of description, "reflector" or "mirror" can be used interchangeably to refer to an optical element and/or a surface having a reflectivity greater than or equal to about 0.01% and less than or equal to 100%. For example, an optical element and/or a surface having a reflectivity greater than or equal to about 5% and less than or equal to 99%, greater than or equal to about 10% and less than or equal to 90%, greater than or equal to about 15% and less than or equal to 80%, greater than or equal to about 20% and less than or equal to 70%, greater than or equal to about 30% and less than or equal to 60%, or any value in any range/sub-range defined by these values can be considered as a reflector or mirror.

What is claimed is:

1. A sensing system configured to analyze constituents in a gas flow, the sensing system comprising:
  a light emitter configured to emit at least one beam of light;
  a sample chamber adapted for supporting interaction of the beam of light received from the light emitter with the gas flow;
  a first light detector;
  a second light detector; and
  a beam splitter configured to transform a first portion of the beam of light transmitted through the sample chamber into a first convergent beam of light and a second portion of the beam of light transmitted through the sample chamber into a second convergent beam of light.

2. The sensing system according to claim 1, wherein the beam splitter comprises a first plurality of reflecting surfaces configured to transform the first portion of the beam of light transmitted through the sample chamber and to redirect the first convergent beam of light on the first light detector; and a second plurality of reflecting surfaces configured to transform the second portion of the beam of light transmitted through the sample chamber and to redirect the second convergent beam of light on the second light detector.

3. The sensing system according to claim 2, wherein the sensing system is configured to generate a differential signal using a first signal received from the first light detector and a second signal received from the second light detector.

4. The sensing system according to claim 3, wherein the differential signal is a linear or non-linear function of the first signal and the second signal, and wherein the differential signal is usable for estimating a concentration of a target gas molecule in the sample chamber.

5. The sensing system according to claim 4, wherein the light emitter is configured to emit light within a wavelength interval including at least one absorption wavelength band of the target gas molecule.

6. The sensing system according to claim 4, wherein the first light detector is covered by a first filter, wherein the first filter transmits light having wavelengths within at least one of absorption wavelength bands of the target gas molecule.

7. The sensing system according to claim 6, wherein the target gas molecule is carbon dioxide.

8. The sensing system according to claim 7, wherein the absorption wavelength band of the target gas molecule is located near 4.2 micrometer.

9. The sensing system according to claim 4, wherein the second light detector is covered by a second filter, wherein the second filter transmits light having wavelengths not overlapping with any of absorption wavelength bands of the target gas molecule.

10. The sensing system according to claim 2, wherein an area of an illuminated region on each light detector by the first or second portion of beam of light transmitted through the sample chamber, is smaller than a sensitive area of the respective light detector.

11. The sensing system according to claim 1, further comprising a collimator configured to transform the beam of light generated by the light emitter to a collimated beam of light passing through the sample chamber.

12. The sensing system according to claim 1, wherein the light emitter is a thermal emitter.

13. The sensing system according to claim 1, further comprising an airway adapter wherein the airway adapter comprises:
  a gas entrance port and a gas exit port;
  the sample chamber, wherein the sample chamber is configured to support gas flow along a longitudinal direction from the gas entrance port to the gas exit port;
  an entrance window; and
  an exit window to allow transmission of light through the sample chamber along a transverse direction perpendicular to the longitudinal direction.

14. A spectrometer configured to analyze constituents in a gas flow, the spectrometer comprising:
  a light emitter configured to emit at least one beam of light;
  a sample chamber adapted for supporting interaction of the beam of light received from the light emitter with the gas flow;
  a first light detector;
  a second light detector; and
  a reflective beam splitter configured to:
    divide the beam of light transmitted through the sample chamber into a first and a second convergent beams of light.

15. The spectrometer according to claim 14, wherein the spectrometer is configured to generate a differential signal using a first signal received from the first light detector and a second signal received from the second light detector, wherein the differential signal is usable for estimating a concentration of a target gas molecule in the sample chamber.

16. The spectrometer according to claim 15, wherein in the absence of the target gas molecule in the sample chamber, a difference between optical power carried by the first beam of light and optical power carried by the second beam of light is less than 5% of total optical power carried by the beam of light emitted by the light emitter.

17. The spectrometer according to claim 15, wherein the target gas molecule is a carbon dioxide molecule.

18. The spectrometer according to claim 14, further comprising an off-axis parabolic mirror configured to transform the beam of light generated by the light emitter to a collimated beam of light passing through the sample chamber before being divided by the beam splitter.

19. The spectrometer according to claim 14, wherein the beam splitter is configured to focus the first and second convergent beams of light on the first and second light detectors, respectively.

20. The spectrometer according to claim 19, wherein the beam splitter is a concave segmented reflective beam splitter.

* * * * *